(12) United States Patent
Latz et al.

(10) Patent No.: US 7,723,054 B2
(45) Date of Patent: May 25, 2010

(54) TOLL-LIKE RECEPTOR 9 MODULATORS

(75) Inventors: Eicke Latz, Boston, MA (US); Alberto Visintin, Worcester, MA (US); Douglas T. Golenbock, Wellesley, MA (US)

(73) Assignee: University of Massachusetts, Boston, MA (US)

( * ) Notice: Subject to any disclaimer, the term of this patent is extended or adjusted under 35 U.S.C. 154(b) by 306 days.

(21) Appl. No.: 11/341,319

(22) Filed: Jan. 26, 2006

(65) Prior Publication Data

US 2006/0127884 A1    Jun. 15, 2006

Related U.S. Application Data

(63) Continuation of application No. 11/014,367, filed on Dec. 16, 2004, now abandoned.

(60) Provisional application No. 60/530,115, filed on Dec. 16, 2003, provisional application No. 60/530,699, filed on Dec. 16, 2003.

(51) Int. Cl.
*G01N 33/52* (2006.01)
*G01N 33/53* (2006.01)
*G01N 33/557* (2006.01)
*G01N 33/566* (2006.01)
*G01N 33/58* (2006.01)

(52) U.S. Cl. ............... 435/7.21; 435/7.8; 435/69.7; 530/350; 530/402; 530/412; 536/23.4; 536/23.5; 536/22.1

(58) Field of Classification Search ............... None
See application file for complete search history.

(56) References Cited

U.S. PATENT DOCUMENTS

2003/0104523 A1    6/2003    Bauer et al.

FOREIGN PATENT DOCUMENTS

WO    WO 03/035695 A2  *  5/2003

OTHER PUBLICATIONS

Ahmad-Nejad et al., "Bacterial CpG-DNA and lipopolysaccharides activate Toll-like receptors at distinct cellular compartments," *Eur. J. Immunol.*, 32:1958-1968 (2002).
Agrawal and Kandimalla, "Medicinal chemistry and therapeutic potential of CpG DNA," *Trends Mol. Med.* 8(3):114-21 (2002).
Akira, "Mammalian Toll-like Receptors," *Curr. Opin. Immunol.*, 15:5-11 (2003).
Anders et al., "Activation of toll-like receptor-9 induces progression of renal disease in MRL-Fas(lpr) mice," *FASEB. J.* 18(3):534-536 (2004).
Bauer et al., "Human TLR9 confers responsiveness to bacterial DNA via species-specific CpG motif recognition," *Proc. Natl. Acad. Sci. USA*, 98: 9237-9242 (2001).
Chan et al., A domain in TNF receptors that mediates ligand-independent receptor assembly and signaling, *Science*, 288(5475):2351-2354 (2000).
Chow et al., "Dendritic cell maturation triggers retrograde MHC class II transport from lysosomes to the plasma membrane," *Nature*, 418:988-994 (2002).
Gordon, "Pattern recognition receptors: doubling up for the innate immune response," *Cell*, 111(7):927-930 (2002).
Hirschfeld et al., "Cutting Edge: Repurification of Lipopolysaccharide Eliminates Signaling Through Both Human and Murine Toll-Like Receptor 2," *The Journal of Immunology*, 165:618-622 (2000).
Hornung et al., "Quantitative Expression of Toll-Like Receptor 1-10 mRNA in Cellular Subsets of Human peripheral Blood Mononuclear Cells and Sensitivity to CpG Oligodeoxynucleotides," *J. Immunol.*, 168:4531-4537 (2002).
Kadowaki et al., "Subsets of Human Dendritic Cell Precursors Express Different Toll-like Receptors and Respond to Different Microbial Antigens," *J. Exp. Med.*, 194:863-869 (2001).
Krieg, "CpG motifs in bacterial DNA and their immune effects," Annu. Rev. Immunol. 20:709-60 (2002).
Latz et al., "Lipopolysaccharide rapidly traffics to and from the Golgi apparatus with the toll-like receptor 4-MD-2-CD14 complex in a process that is distinct from the initiation of signal transduction," J. Biol. Chem. 277(49):47834-43 (2002).
Latz et al., "TLR9 signals after translocating from the ER to CpG DNA in the lysosome," Nat. Immunol. 5(2):190-8 (2004).
Mellman, "Endocytosis and Molecular Sorting," *Annu. Rev. Cell. Dev. Biol.*, 12:575-625 (1996).
Rachmilewitz et al., "Toll-Like Receptor 9 Signaling Mediates the Anti-Inflammatory Effects of Probiotics in Murine Experimental Colitis," *Gastroenterology*, 126(2):520-528 (2004).
Takeshita et al., "Cutting edge: Role of Toll-like receptor 9 in CpG DNA-induced activation of human cells," J Immunol. 167(7):3555-8 (2001).
Tauszig et al., "Toll-related receptors and the control of antimicrobial peptide expression in *Drosophila*," Proc. Natl. Acad. Sci. USA 97(19):10520-5 (2000).
Visintin et al., "Secreted MD-2 is a large polymeric protein that efficiently confers lipopolysaccharide sensitivity to Toll-like receptor 4," Proc. Natl. Acad. Sci. USA 98(21):12156-61 (2001).
Weber et al., "Binding of the *Drosophila* cytokine Spatzle to Toll is direct and establishes signaling," Nat. Immunol. 4(8):794-800 (2003).
Whitmore et al., "Systemic administration of LPD prepared with CpG oligonucleotides inhibits the growth of established pulmonary metastases by stimulating innate and acquired antitumor immune responses," Cancer Immunol. Immunother. 50(10):503-14 (2001).
Swanson et al., "Tubular Lysosomes Accompany Stimulated Pinocytosis in Macrophages," *The Journal of Cell Biology*, 104: 1217-1222 (1987).

* cited by examiner

*Primary Examiner*—Lorraine Spector
*Assistant Examiner*—Claire Kaufman
(74) *Attorney, Agent, or Firm*—Fish & Richardson P.C.

(57) ABSTRACT

TLR9 is localized to endoplasmic reticulum and upon stimulation with a TLR9 ligand, is transported to a tubular lysosomal compartment as is CpG-DNA. Furthermore, it is shown that TLR9 and CpG-DNA directly bind. It was also found that the MyD88 translocates in response to activation of TLR9-mediated signaling. Methods of identifying compounds that affect translocation and activity of TLR9 and MyD88 are described.

13 Claims, 8 Drawing Sheets
(8 of 8 Drawing Sheet(s) Filed in Color)

Figure 3A   Figure 3B   Figure 3C   Figure 3D
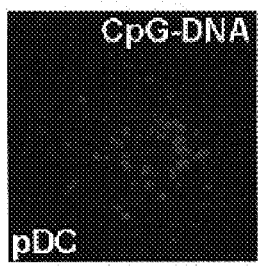  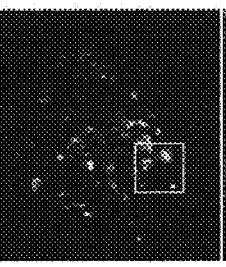 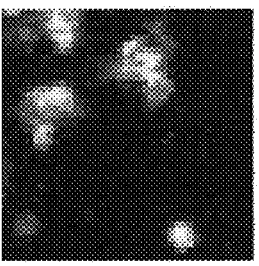
Figure 3E   Figure 3F   Figure 3G   Figure 3H
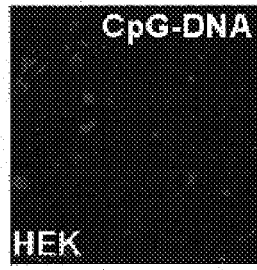  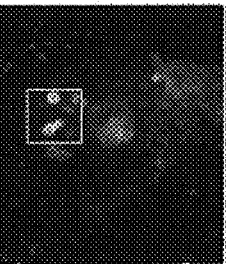 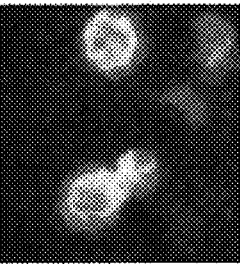
Figure 3I   Figure 3J   Figure 3K   Figure 3L
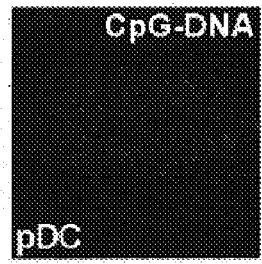  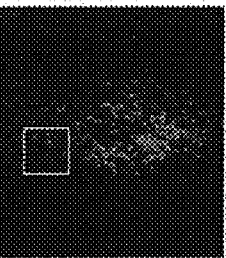 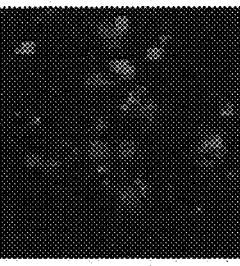
Figure 3M   Figure 3N   Figure 3O   Figure 3P
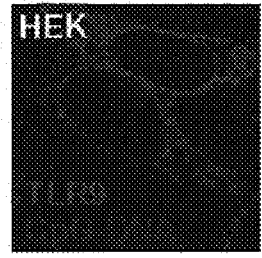  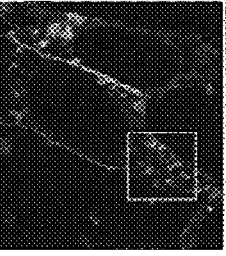 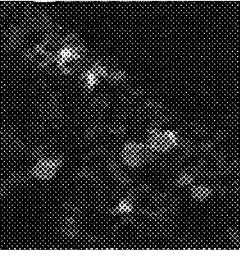

Figure 9A
No stimulation
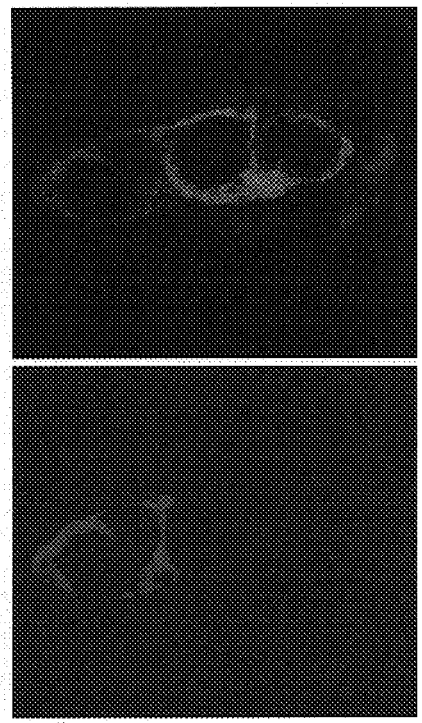
Figure 9C
Figure 9B
CpG DNA (15 min)
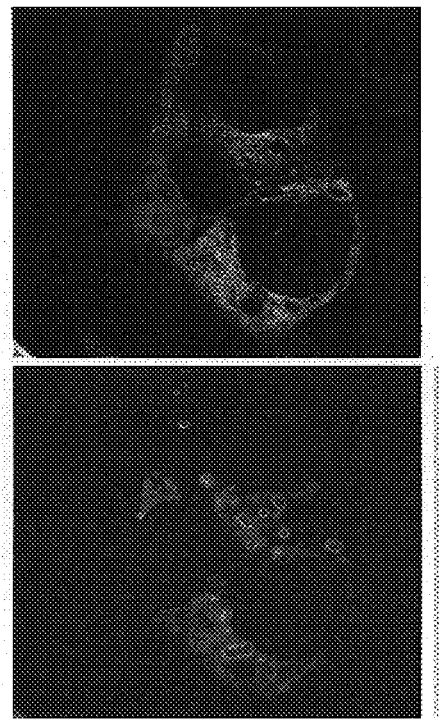
Figure 9D

SEQUENCE LISTING

<160> NUMBER OF SEQ ID NOS: 11

<210> SEQ ID NO 1
<211> LENGTH: 1032
<212> TYPE: PRT
<213> ORGANISM: Homo sapiens

<400> SEQUENCE: 1

```
Met Gly Phe Cys Arg Ser Ala Leu His Pro Leu Ser Leu Leu Val Gln
 1               5                  10                  15

Ala Ile Met Leu Ala Met Thr Leu Ala Leu Gly Thr Leu Pro Ala Phe
            20                  25                  30

Leu Pro Cys Glu Leu Gln Pro His Gly Leu Val Asn Cys Asn Trp Leu
        35                  40                  45

Phe Leu Lys Ser Val Pro His Phe Ser Met Ala Ala Pro Arg Gly Asn
    50                  55                  60

Val Thr Ser Leu Ser Leu Ser Ser Asn Arg Ile His His Leu His Asp
 65                  70                  75                  80

Ser Asp Phe Ala His Leu Pro Ser Leu Arg His Leu Asn Leu Lys Trp
                85                  90                  95

Asn Cys Pro Pro Val Gly Leu Ser Pro Met His Phe Pro Cys His Met
           100                 105                 110

Thr Ile Glu Pro Ser Thr Phe Leu Ala Val Pro Thr Leu Glu Glu Leu
       115                 120                 125

Asn Leu Ser Tyr Asn Asn Ile Met Thr Val Pro Ala Leu Pro Lys Ser
   130                 135                 140

Leu Ile Ser Leu Ser Leu Ser His Thr Asn Ile Leu Met Leu Asp Ser
145                 150                 155                 160

Ala Ser Leu Ala Gly Leu His Ala Leu Arg Phe Leu Phe Met Asp Gly
                165                 170                 175

Asn Cys Tyr Tyr Lys Asn Pro Cys Arg Gln Ala Leu Glu Val Ala Pro
            180                 185                 190

Gly Ala Leu Leu Gly Leu Gly Asn Leu Thr His Leu Ser Leu Lys Tyr
        195                 200                 205

Asn Asn Leu Thr Val Val Pro Arg Asn Leu Pro Ser Ser Leu Glu Tyr
    210                 215                 220

Leu Leu Leu Ser Tyr Asn Arg Ile Val Lys Leu Ala Pro Glu Asp Leu
225                 230                 235                 240

Ala Asn Leu Thr Ala Leu Arg Val Leu Asp Val Gly Gly Asn Cys Arg
                245                 250                 255

Arg Cys Asp His Ala Pro Asn Pro Cys Met Glu Cys Pro Arg His Phe
            260                 265                 270

Pro Gln Leu His Pro Asp Thr Phe Ser His Leu Ser Arg Leu Glu Gly
        275                 280                 285

Leu Val Leu Lys Asp Ser Ser Leu Ser Trp Leu Asn Ala Ser Trp Phe
    290                 295                 300

Arg Gly Leu Gly Asn Leu Arg Val Leu Asp Leu Ser Glu Asn Phe Leu
305                 310                 315                 320

Tyr Lys Cys Ile Thr Lys Thr Lys Ala Phe Gln Gly Leu Thr Gln Leu
                325                 330                 335

Arg Lys Leu Asn Leu Ser Phe Asn Tyr Gln Lys Arg Val Ser Phe Ala
            340                 345                 350

His Leu Ser Leu Ala Pro Ser Phe Gly Ser Leu Val Ala Leu Lys Glu
```

```
            355                 360                 365
Leu Asp Met His Gly Ile Phe Phe Arg Ser Leu Asp Glu Thr Thr Leu
    370                 375                 380

Arg Pro Leu Ala Arg Leu Pro Met Leu Gln Thr Leu Arg Leu Gln Met
385                 390                 395                 400

Asn Phe Ile Asn Gln Ala Gln Leu Gly Ile Phe Arg Ala Phe Pro Gly
                405                 410                 415

Leu Arg Tyr Val Asp Leu Ser Asp Asn Arg Ile Ser Gly Ala Ser Glu
                420                 425                 430

Leu Thr Ala Thr Met Gly Glu Ala Asp Gly Glu Lys Val Trp Leu
        435                 440                 445

Gln Pro Gly Asp Leu Ala Pro Ala Pro Val Asp Thr Pro Ser Ser Glu
    450                 455                 460

Asp Phe Arg Pro Asn Cys Ser Thr Leu Asn Phe Thr Leu Asp Leu Ser
465                 470                 475                 480

Arg Asn Asn Leu Val Thr Val Gln Pro Glu Met Phe Ala Gln Leu Ser
                485                 490                 495

His Leu Gln Cys Leu Arg Leu Ser His Asn Cys Ile Ser Gln Ala Val
            500                 505                 510

Asn Gly Ser Gln Phe Leu Pro Leu Thr Gly Leu Gln Val Leu Asp Leu
        515                 520                 525

Ser His Asn Lys Leu Asp Leu Tyr His Glu His Ser Phe Thr Glu Leu
    530                 535                 540

Pro Arg Leu Glu Ala Leu Asp Leu Ser Tyr Asn Ser Gln Pro Phe Gly
545                 550                 555                 560

Met Gln Gly Val Gly His Asn Phe Ser Phe Val Ala His Leu Arg Thr
                565                 570                 575

Leu Arg His Leu Ser Leu Ala His Asn Asn Ile His Ser Gln Val Ser
            580                 585                 590

Gln Gln Leu Cys Ser Thr Ser Leu Arg Ala Leu Asp Phe Ser Gly Asn
        595                 600                 605

Ala Leu Gly His Met Trp Ala Glu Gly Asp Leu Tyr Leu His Phe Phe
    610                 615                 620

Gln Gly Leu Ser Gly Leu Ile Trp Leu Asp Leu Ser Gln Asn Arg Leu
625                 630                 635                 640

His Thr Leu Leu Pro Gln Thr Leu Arg Asn Leu Pro Lys Ser Leu Gln
                645                 650                 655

Val Leu Arg Leu Arg Asp Asn Tyr Leu Ala Phe Phe Lys Trp Trp Ser
            660                 665                 670

Leu His Phe Leu Pro Lys Leu Glu Val Leu Asp Leu Ala Gly Asn Gln
    675                 680                 685

Leu Lys Ala Leu Thr Asn Gly Ser Leu Pro Ala Gly Thr Arg Leu Arg
690                 695                 700

Arg Leu Asp Val Ser Cys Asn Ser Ile Ser Phe Val Ala Pro Gly Phe
705                 710                 715                 720

Phe Ser Lys Ala Lys Glu Leu Arg Glu Leu Asn Leu Ser Ala Asn Ala
                725                 730                 735

Leu Lys Thr Val Asp His Ser Trp Phe Gly Pro Leu Ala Ser Ala Leu
            740                 745                 750

Gln Ile Leu Asp Val Ser Ala Asn Pro Leu His Cys Ala Cys Gly Ala
        755                 760                 765

Ala Phe Met Asp Phe Leu Leu Glu Val Gln Ala Ala Val Pro Gly Leu
    770                 775                 780
```

-continued

```
Pro Ser Arg Val Lys Cys Gly Ser Pro Gly Gln Leu Gln Gly Leu Ser
785                 790                 795                 800

Ile Phe Ala Gln Asp Leu Arg Leu Cys Leu Asp Glu Ala Leu Ser Trp
                805                 810                 815

Asp Cys Phe Ala Leu Ser Leu Ala Val Ala Leu Gly Leu Gly Val
            820                 825                 830

Pro Met Leu His His Leu Cys Gly Trp Asp Leu Trp Tyr Cys Phe His
            835                 840                 845

Leu Cys Leu Ala Trp Leu Pro Trp Arg Gly Arg Gln Ser Gly Arg Asp
850                 855                 860

Glu Asp Ala Leu Pro Tyr Asp Ala Phe Val Val Phe Asp Lys Thr Gln
865                 870                 875                 880

Ser Ala Val Ala Asp Trp Val Tyr Asn Glu Leu Arg Gly Gln Leu Glu
                885                 890                 895

Glu Cys Arg Gly Arg Trp Ala Leu Arg Leu Cys Leu Glu Glu Arg Asp
            900                 905                 910

Trp Leu Pro Gly Lys Thr Leu Phe Glu Asn Leu Trp Ala Ser Val Tyr
        915                 920                 925

Gly Ser Arg Lys Thr Leu Phe Val Leu Ala His Thr Asp Arg Val Ser
930                 935                 940

Gly Leu Leu Arg Ala Ser Phe Leu Leu Ala Gln Gln Arg Leu Leu Glu
945                 950                 955                 960

Asp Arg Lys Asp Val Val Val Leu Val Ile Leu Ser Pro Asp Gly Arg
                965                 970                 975

Arg Ser Arg Tyr Val Arg Leu Arg Gln Arg Leu Cys Arg Gln Ser Val
            980                 985                 990

Leu Leu Trp Pro His Gln Pro Ser Gly Gln Arg Ser Phe Trp Ala Gln
        995                 1000                1005

Leu Gly Met Ala Leu Thr Arg Asp Asn His His Phe Tyr Asn Arg Asn
    1010                1015                1020

Phe Cys Gln Gly Pro Thr Ala Glu
1025                1030

<210> SEQ ID NO 2
<211> LENGTH: 1032
<212> TYPE: PRT
<213> ORGANISM: Mus musculus

<400> SEQUENCE: 2

Met Val Leu Arg Arg Arg Thr Leu His Pro Leu Ser Leu Leu Val Gln
1               5                   10                  15

Ala Ala Val Leu Ala Glu Thr Leu Ala Leu Gly Thr Leu Pro Ala Phe
            20                  25                  30

Leu Pro Cys Glu Leu Lys Pro His Gly Leu Val Asp Cys Asn Trp Leu
        35                  40                  45

Phe Leu Lys Ser Val Pro Arg Phe Ser Ala Ala Ala Ser Cys Ser Asn
    50                  55                  60

Ile Thr Arg Leu Ser Leu Ile Ser Asn Arg Ile His His Leu His Asn
65                  70                  75                  80

Ser Asp Phe Val His Leu Ser Asn Leu Arg Gln Leu Asn Leu Lys Trp
                85                  90                  95

Asn Cys Pro Pro Thr Gly Leu Ser Pro Leu His Phe Ser Cys His Met
            100                 105                 110

Thr Ile Glu Pro Arg Thr Phe Leu Ala Met Arg Thr Leu Glu Glu Leu
```

```
            115                 120                 125
Asn Leu Ser Tyr Asn Gly Ile Thr Thr Val Pro Arg Leu Pro Ser Ser
    130                 135                 140

Leu Val Asn Leu Ser Leu Ser His Thr Asn Ile Leu Val Leu Asp Ala
145                 150                 155                 160

Asn Ser Leu Ala Gly Leu Tyr Ser Leu Arg Val Leu Phe Met Asp Gly
                165                 170                 175

Asn Cys Tyr Tyr Lys Asn Pro Cys Thr Gly Ala Val Lys Val Thr Pro
            180                 185                 190

Gly Ala Leu Leu Gly Leu Ser Asn Leu Thr His Leu Ser Leu Lys Tyr
                195                 200                 205

Asn Asn Leu Thr Lys Val Pro Arg Gln Leu Pro Pro Ser Leu Glu Tyr
    210                 215                 220

Leu Leu Val Ser Tyr Asn Leu Ile Val Lys Leu Gly Pro Glu Asp Leu
225                 230                 235                 240

Ala Asn Leu Thr Ser Leu Arg Val Leu Asp Val Gly Gly Asn Cys Arg
                245                 250                 255

Arg Cys Asp His Ala Pro Asn Pro Cys Ile Glu Cys Gly Gln Lys Ser
            260                 265                 270

Leu His Leu His Pro Glu Thr Phe His His Leu Ser His Leu Glu Gly
    275                 280                 285

Leu Val Leu Lys Asp Ser Ser Leu His Thr Leu Asn Ser Ser Trp Phe
    290                 295                 300

Gln Gly Leu Val Asn Leu Ser Val Leu Asp Leu Ser Glu Asn Phe Leu
305                 310                 315                 320

Tyr Glu Ser Ile Asn His Thr Asn Ala Phe Gln Asn Leu Thr Arg Leu
                325                 330                 335

Arg Lys Leu Asn Leu Ser Phe Asn Tyr Arg Lys Lys Val Ser Phe Ala
            340                 345                 350

Arg Leu His Leu Ala Ser Ser Phe Lys Asn Leu Val Ser Leu Gln Glu
    355                 360                 365

Leu Asn Met Asn Gly Ile Phe Phe Arg Ser Leu Asn Lys Tyr Thr Leu
    370                 375                 380

Arg Trp Leu Ala Asp Leu Pro Lys Leu His Thr Leu His Leu Gln Met
385                 390                 395                 400

Asn Phe Ile Asn Gln Ala Gln Leu Ser Ile Phe Gly Thr Phe Arg Ala
                405                 410                 415

Leu Arg Phe Val Asp Leu Ser Asp Asn Arg Ile Ser Gly Pro Ser Thr
            420                 425                 430

Leu Ser Glu Ala Thr Pro Glu Glu Ala Asp Asp Ala Glu Gln Glu Glu
    435                 440                 445

Leu Leu Ser Ala Asp Pro His Pro Ala Pro Leu Ser Thr Pro Ala Ser
    450                 455                 460

Lys Asn Phe Met Asp Arg Cys Lys Asn Phe Lys Phe Thr Met Asp Leu
465                 470                 475                 480

Ser Arg Asn Asn Leu Val Thr Ile Lys Pro Glu Met Phe Val Asn Leu
                485                 490                 495

Ser Arg Leu Gln Cys Leu Ser Leu Ser His Asn Ser Ile Ala Gln Ala
            500                 505                 510

Val Asn Gly Ser Gln Phe Leu Pro Leu Thr Asn Leu Gln Val Leu Asp
    515                 520                 525

Leu Ser His Asn Lys Leu Asp Leu Tyr His Trp Lys Ser Phe Ser Glu
    530                 535                 540
```

```
Leu Pro Gln Leu Gln Ala Leu Asp Leu Ser Tyr Asn Ser Gln Pro Phe
545                 550                 555                 560

Ser Met Lys Gly Ile Gly His Asn Phe Ser Phe Val Thr His Leu Ser
            565                 570                 575

Met Leu Gln Ser Leu Ser Leu Ala His Asn Asp Ile His Thr Arg Val
                580                 585                 590

Ser Ser His Leu Asn Ser Asn Ser Val Arg Phe Leu Asp Phe Ser Gly
            595                 600                 605

Asn Gly Met Gly Arg Met Trp Asp Glu Gly Gly Leu Tyr Leu His Phe
            610                 615                 620

Phe Gln Gly Leu Ser Gly Leu Leu Lys Leu Asp Leu Ser Gln Asn Asn
625                 630                 635                 640

Leu His Ile Leu Arg Pro Gln Asn Leu Asp Asn Leu Pro Lys Ser Leu
            645                 650                 655

Lys Leu Leu Ser Leu Arg Asp Asn Tyr Leu Ser Phe Phe Asn Trp Thr
            660                 665                 670

Ser Leu Ser Phe Leu Pro Asn Leu Glu Val Leu Asp Leu Ala Gly Asn
            675                 680                 685

Gln Leu Lys Ala Leu Thr Asn Gly Thr Leu Pro Asn Gly Thr Leu Leu
690                 695                 700

Gln Lys Leu Asp Val Ser Ser Asn Ser Ile Val Ser Val Val Pro Ala
705                 710                 715                 720

Phe Phe Ala Leu Ala Val Glu Leu Lys Glu Val Asn Leu Ser His Asn
                725                 730                 735

Ile Leu Lys Thr Val Asp Arg Ser Trp Phe Gly Pro Ile Val Met Asn
            740                 745                 750

Leu Thr Val Leu Asp Val Arg Ser Asn Pro Leu His Cys Ala Cys Gly
            755                 760                 765

Ala Ala Phe Val Asp Leu Leu Leu Glu Val Gln Thr Lys Val Pro Gly
770                 775                 780

Leu Ala Asn Gly Val Lys Cys Gly Ser Pro Gly Gln Leu Gln Gly Arg
785                 790                 795                 800

Ser Ile Phe Ala Gln Asp Leu Arg Leu Cys Leu Asp Glu Val Leu Ser
                805                 810                 815

Trp Asp Cys Phe Gly Leu Ser Leu Leu Ala Val Ala Val Gly Met Val
            820                 825                 830

Val Pro Ile Leu His His Leu Cys Gly Trp Asp Val Trp Tyr Cys Phe
            835                 840                 845

His Leu Cys Leu Ala Trp Leu Pro Leu Leu Ala Arg Ser Arg Arg Ser
850                 855                 860

Ala Gln Thr Leu Pro Tyr Asp Ala Phe Val Val Phe Asp Lys Ala Gln
865                 870                 875                 880

Ser Ala Val Ala Asp Trp Val Tyr Asn Glu Leu Arg Val Arg Leu Glu
                885                 890                 895

Glu Arg Arg Gly Arg Arg Ala Leu Arg Leu Cys Leu Glu Asp Arg Asp
            900                 905                 910

Trp Leu Pro Gly Gln Thr Leu Phe Glu Asn Leu Trp Ala Ser Ile Tyr
            915                 920                 925

Gly Ser Arg Lys Thr Leu Phe Val Leu Ala His Thr Asp Arg Val Ser
            930                 935                 940

Gly Leu Leu Arg Thr Ser Phe Leu Leu Ala Gln Gln Arg Leu Leu Glu
945                 950                 955                 960
```

```
Asp Arg Lys Asp Val Val Leu Val Ile Leu Arg Pro Asp Ala His
            965             970             975

Arg Ser Arg Tyr Val Arg Leu Arg Gln Arg Leu Cys Arg Gln Ser Val
            980             985             990

Leu Phe Trp Pro Gln Gln Pro Asn Gly Gln Gly Gly Phe Trp Ala Gln
            995             1000            1005

Leu Ser Thr Ala Leu Thr Arg Asp Asn Arg His Phe Tyr Asn Gln Asn
            1010            1015            1020

Phe Cys Arg Gly Pro Thr Ala Glu
1025            1030

<210> SEQ ID NO 3
<211> LENGTH: 1032
<212> TYPE: PRT
<213> ORGANISM: Rattus norvegicus

<400> SEQUENCE: 3

Met Val Leu Cys Ser Arg Thr Leu His Pro Leu Ser Leu Leu Val Gln
 1               5                  10                  15

Ala Ala Val Leu Ala Glu Ala Leu Ala Leu Gly Thr Leu Pro Ala Phe
                20                  25                  30

Leu Pro Cys Glu Leu Lys Pro His Gly Leu Val Asp Cys Asn Trp Leu
                35                  40                  45

Phe Leu Lys Ser Val Pro His Phe Ser Ala Ala Glu Pro Arg Ser Asn
            50                  55                  60

Ile Thr Ser Leu Ser Leu Ile Ala Asn Arg Ile His His Leu His Asn
65                  70                  75                  80

Leu Asp Phe Val His Leu Pro Asn Val Arg Gln Leu Asn Leu Lys Trp
                85                  90                  95

Asn Cys Pro Pro Pro Gly Leu Ser Pro Leu His Phe Ser Cys Arg Met
                100                 105                 110

Thr Ile Glu Pro Lys Thr Phe Leu Ala Met Arg Met Leu Glu Glu Leu
                115                 120                 125

Asn Leu Ser Tyr Asn Gly Ile Thr Thr Val Pro Arg Leu Pro Ser Ser
            130                 135                 140

Leu Thr Asn Leu Ser Leu Ser His Thr Asn Ile Leu Val Leu Asp Ala
145                 150                 155                 160

Ser Ser Leu Ala Gly Leu His Ser Leu Arg Val Leu Phe Met Asp Gly
                165                 170                 175

Asn Cys Tyr Tyr Lys Asn Pro Cys Asn Gly Ala Val Asn Val Thr Pro
                180                 185                 190

Asp Ala Phe Leu Gly Leu Ser Asn Leu Thr His Leu Ser Leu Lys Tyr
                195                 200                 205

Asn Asn Leu Thr Glu Val Pro Arg Gln Leu Pro Pro Ser Leu Glu Tyr
            210                 215                 220

Leu Leu Leu Ser Tyr Asn Leu Ile Val Lys Leu Gly Pro Glu Asp Leu
225                 230                 235                 240

Ala Asn Leu Thr Ser Leu Arg Val Leu Asp Val Gly Gly Asn Cys Arg
                245                 250                 255

Arg Cys Asp His Ala Pro Asp Leu Cys Thr Glu Cys Arg Gln Lys Ser
                260                 265                 270

Leu Asp Leu His Pro Gln Thr Phe His His Leu Ser His Leu Glu Gly
            275                 280                 285

Leu Val Leu Lys Asp Ser Ser Leu His Ser Leu Asn Ser Lys Trp Phe
            290                 295                 300
```

```
Gln Gly Leu Val Asn Leu Ser Val Leu Asp Leu Ser Glu Asn Phe Leu
305                 310                 315                 320

Tyr Glu Ser Ile Asn Lys Thr Ser Ala Phe Gln Asn Leu Thr Arg Leu
                325                 330                 335

Arg Lys Leu Asp Leu Ser Phe Asn Tyr Cys Lys Lys Val Ser Phe Ala
                340                 345                 350

Arg Leu His Leu Ala Ser Ser Phe Lys Ser Leu Val Ser Leu Gln Glu
                355                 360                 365

Leu Asn Met Asn Gly Ile Phe Phe Arg Leu Leu Asn Lys Asn Thr Leu
            370                 375                 380

Arg Trp Leu Ala Gly Leu Pro Lys Leu His Thr Leu His Leu Gln Met
385                 390                 395                 400

Asn Phe Ile Asn Gln Ala Gln Leu Ser Val Phe Ser Thr Phe Arg Ala
                405                 410                 415

Leu Arg Phe Val Asp Leu Ser Asn Asn Arg Ile Ser Gly Pro Pro Thr
                420                 425                 430

Leu Ser Arg Val Ala Pro Glu Lys Ala Asp Glu Ala Glu Lys Gly Val
            435                 440                 445

Pro Trp Pro Ala Ser Leu Thr Pro Ala Leu Pro Ser Thr Pro Val Ser
450                 455                 460

Lys Asn Phe Met Val Arg Cys Lys Asn Leu Arg Phe Thr Met Asp Leu
465                 470                 475                 480

Ser Arg Asn Asn Leu Val Thr Ile Lys Pro Glu Met Phe Val Asn Leu
                485                 490                 495

Ser His Leu Gln Cys Leu Ser Leu Ser His Asn Cys Ile Ala Gln Ala
            500                 505                 510

Val Asn Gly Ser Gln Phe Leu Pro Leu Thr Asn Leu Lys Val Leu Asp
            515                 520                 525

Leu Ser Tyr Asn Lys Leu Asp Leu Tyr His Ser Lys Ser Phe Ser Glu
530                 535                 540

Leu Pro Gln Leu Gln Ala Leu Asp Leu Ser Tyr Asn Ser Gln Pro Phe
545                 550                 555                 560

Ser Met Gln Gly Ile Gly His Asn Phe Ser Phe Leu Ala Asn Leu Ser
                565                 570                 575

Arg Leu Gln Asn Leu Ser Leu Ala His Asn Asp Ile His Ser Arg Val
                580                 585                 590

Ser Ser Arg Leu Tyr Ser Thr Ser Val Glu Tyr Leu Asp Phe Ser Gly
            595                 600                 605

Asn Gly Val Gly Arg Met Trp Asp Glu Glu Asp Leu Tyr Leu Tyr Phe
610                 615                 620

Phe Gln Asp Leu Arg Ser Leu Ile His Leu Asp Leu Ser Gln Asn Lys
625                 630                 635                 640

Leu His Ile Leu Arg Pro Gln Asn Leu Asn Tyr Leu Pro Lys Ser Leu
                645                 650                 655

Thr Lys Leu Ser Phe Arg Asp Asn His Leu Ser Phe Phe Asn Trp Ser
                660                 665                 670

Ser Leu Ala Phe Leu Pro Asn Leu Arg Asp Leu Asp Leu Ala Gly Asn
            675                 680                 685

Leu Leu Lys Ala Leu Thr Asn Gly Thr Leu Pro Asn Gly Thr Leu Leu
            690                 695                 700

Gln Lys Leu Asp Val Ser Ser Asn Ser Ile Val Phe Val Val Pro Ala
705                 710                 715                 720
```

-continued

```
Phe Phe Ala Leu Ala Val Glu Leu Lys Glu Val Asn Leu Ser His Asn
                725                 730                 735

Ile Leu Lys Thr Val Asp Arg Ser Trp Phe Gly Pro Ile Val Met Asn
            740                 745                 750

Leu Thr Val Leu Asp Val Ser Ser Asn Pro Leu His Cys Ala Cys Gly
        755                 760                 765

Ala Pro Phe Val Asp Leu Leu Leu Glu Val Gln Thr Lys Val Pro Gly
    770                 775                 780

Leu Ala Asn Gly Val Lys Cys Gly Ser Pro Arg Gln Leu Gln Gly Arg
785                 790                 795                 800

Ser Ile Phe Ala Gln Asp Leu Arg Leu Cys Leu Asp Asp Val Leu Ser
                805                 810                 815

Arg Asp Cys Phe Gly Leu Ser Leu Leu Ala Val Ala Val Gly Thr Val
            820                 825                 830

Leu Pro Leu Leu Gln His Leu Cys Gly Trp Asp Val Trp Tyr Cys Phe
        835                 840                 845

His Leu Cys Leu Ala Trp Leu Pro Leu Leu Thr Arg Gly Arg Arg Ser
    850                 855                 860

Ala Gln Ala Leu Pro Tyr Asp Ala Phe Val Val Phe Asp Lys Ala Gln
865                 870                 875                 880

Ser Ala Val Ala Asp Trp Val Tyr Asn Glu Leu Arg Val Arg Leu Glu
                885                 890                 895

Glu Arg Arg Gly Arg Arg Ala Leu Arg Leu Cys Leu Glu Asp Arg Asp
            900                 905                 910

Trp Leu Pro Gly Gln Thr Leu Phe Glu Asn Leu Trp Ala Ser Ile Tyr
        915                 920                 925

Gly Ser Arg Lys Thr Leu Phe Val Leu Ala His Thr Asp Lys Val Ser
    930                 935                 940

Gly Leu Leu Arg Thr Ser Phe Leu Leu Ala Gln Gln Arg Leu Leu Glu
945                 950                 955                 960

Asp Arg Lys Asp Val Val Val Leu Val Ile Leu Arg Pro Asp Ala His
                965                 970                 975

Arg Ser Arg Tyr Val Arg Leu Arg Gln Arg Leu Cys Arg Gln Ser Val
            980                 985                 990

Leu Phe Trp Pro His Gln Pro Asn Gly Gln Gly Ser Phe Trp Ala Gln
        995                 1000                 1005

Leu Ser Thr Ala Leu Thr Arg Asp Asn His His Phe Tyr Asn Arg Asn
    1010                 1015                 1020

Phe Cys Arg Gly Pro Thr Ala Glu
1025                 1030

<210> SEQ ID NO 4
<211> LENGTH: 28
<212> TYPE: DNA
<213> ORGANISM: Artificial Sequence
<220> FEATURE:
<223> OTHER INFORMATION: Primer

<400> SEQUENCE: 4
gaagcaggat ccatgccaca tactttgt                                    28

<210> SEQ ID NO 5
<211> LENGTH: 31
<212> TYPE: DNA
<213> ORGANISM: Artificial Sequence
<220> FEATURE:
<223> OTHER INFORMATION: Primer
```

<400> SEQUENCE: 5
gggctcgagg gactttatcg cagctctcag a                          31

<210> SEQ ID NO 6
<211> LENGTH: 28
<212> TYPE: DNA
<213> ORGANISM: Artificial Sequence
<220> FEATURE:
<223> OTHER INFORMATION: Primer

<400> SEQUENCE: 6
gatgatggat ccatgatgtc tgcctcgc                              28

<210> SEQ ID NO 7
<211> LENGTH: 30
<212> TYPE: DNA
<213> ORGANISM: Artificial Sequence
<220> FEATURE:
<223> OTHER INFORMATION: Primer

<400> SEQUENCE: 7 attttttggct cgaggataga tgttgcttcc                           30

<210> SEQ ID NO 8
<211> LENGTH: 31
<212> TYPE: DNA
<213> ORGANISM: Artificial Sequence
<220> FEATURE:
<223> OTHER INFORMATION: Primer

<400> SEQUENCE: 8
gaagcccctg cccggatcca tgggtttctg c                          31

<210> SEQ ID NO 9
<211> LENGTH: 33
<212> TYPE: DNA
<213> ORGANISM: Artificial Sequence
<220> FEATURE:
<223> OTHER INFORMATION: Primer

<400> SEQUENCE: 9
tccggctcac tcgagttcgg ccgtgggtcc ctg                        33

<210> SEQ ID NO 10
<211> LENGTH: 28
<212> TYPE: DNA
<213> ORGANISM: Artificial Sequence
<220> FEATURE:
<223> OTHER INFORMATION: Primer

<400> SEQUENCE: 10
ccacggggat ccatggctgc aggaggtc                              28

<210> SEQ ID NO 11
<211> LENGTH: 27
<212> TYPE: DNA
<213> ORGANISM: Artificial Sequence
<220> FEATURE:
<223> OTHER INFORMATION: Primer

<400> SEQUENCE: 11
gaacaggtcg acgggcaggg acaaggc                               27

TOLL-LIKE RECEPTOR 9 MODULATORS

CLAIM OF PRIORITY

This application is a continuation of U.S. Utility patent application Ser. No. 11/014,367, filed Dec. 16, 2004 now abandoned which claims priority under 35 USC §119(e) to U.S. Provisional Patent Application Ser. Nos. 60/530,115, and 60/530,699, both filed on Dec. 16, 2003, the entire contents of which are hereby incorporated by reference.

FEDERALLY SPONSORED RESEARCH OR DEVELOPMENT

The U.S. Government has certain rights in this invention pursuant to Grant No. RO1 GM54060 awarded by the National Institute of Health (NIH).

TECHNICAL FIELD

This invention relates to methods of identifying and using modulators of Toll-like receptors.

BACKGROUND

DNA is a microbial product that is sampled by the mammalian immune system. The ability to reproduce the immunostimulatory activity of bacterial DNA with CpG-rich oligonucleotides has led to the elucidation of optimal stimulatory motifs that influence inflammatory activity such as CpG-DNA (Agrawal and Kandimalla, 2002, Trends Mol. Med., 8:114-121; Krieg, 2002, Ann. Rev. Immunol., 20:709-760).

Toll-like receptors (TLRs) are involved in immune system signaling and, depending on the specific TLR, recognize a set of conserved molecular structures (Gordon, 2002, Cell, 111:927-930). TLR9 is a TLR whose signaling is stimulated by CpG-DNA. *Drosophila* Toll acts indirectly, in that it is activated by invasive microorganisms by the pathogen-induced proteolytic processing of prospätzle to spätzle (Tauszig et al., 2000, Proc. Nat. Acad. Sci. U.S.A., 97:10520-10525), the actual Toll-binding ligand (Weber et al., 2003, Nat. Immunol., 4:794-800). It has been reported that TLR9 is expressed intracellularly (Ahmad-Nejad et al., 2002, Eur. J. Immunol., 32:1958-1968; Takeshita et al., 2001, J. Immunol., 167:3555-3558), yet it remains unknown in which subcellular compartment TLR9 is expressed, and in which cellular compartment initiation of TLR9 signaling by CpG-DNA occurs.

SUMMARY

The present invention is based, at least in part, on the discovery that, after addition of CpG-DNA, TLR9 translocates from the endoplasmic reticulum (ER) to a CpG-DNA-containing tubular lysosomal compartment (TLC) for ligand binding and signal transduction. It was also found that TLR9 interacts directly with CpG-DNA. Based on these findings, the invention relates to methods of identifying compounds that are useful for modulating TLR9 signaling, thus affecting, e.g., activation of the innate immune system and related inflammatory responses.

In one aspect, the invention relates to methods of identifying compounds that modulate TLR9 signaling, e.g., by affecting TLR9 localization, translocation, or aggregation. The methods include providing a cell or cells that express a TLR9 polypeptide (e.g., as described herein); contacting the cell with a test compound, thereby providing a test sample; incubating the test sample under conditions and for a time sufficient for TLR9 polypeptide localization, translocation, and/or aggregation to occur in the absence of the test compound; and detecting one or more of TLR9 polypeptide localization, translocation, or aggregation. A difference in TLR9 polypeptide localization, translocation, or aggregation in the test sample, e.g., as compared to TLR9 polypeptide localization, translocation, or aggregation in a reference sample, indicates that the test compound is a compound that affects TLR9 signaling. In some cases, localization of the TLR9 polypeptide, e.g., localization to the endoplasmic reticulum (ER) or to a lysosomal compartment such as the TLC, is affected. In some embodiments, translocation of TLR9 polypeptide, e.g., from the ER to a lysosomal compartment such as the TLC, is affected. In some embodiments, aggregation of TLR9 polypeptide, e.g., in a lysosomal compartment such as the TLC, is affected. In some embodiments, the rate of TLR9 polypeptide localization, translocation, and/or aggregation is affected. Thus, the methods can include determining the localization, translocation, and/or aggregation of TLR9 polypeptide at multiple time points. The test sample can include a TLR9 ligand (e.g., a CpG-DNA or analog thereof).

In some embodiments, the TLR9 polypeptide comprises a full length TLR9 protein or a fragment thereof, e.g., a fragment including comprising one or more regions selected from the group consisting of LRR region 1, LRR region 2; transmembrane domain; Toll/IL-1 Resistance (TIR) domain; a ligand binding domain, e.g., a region including a CXXC motif; e.g., CRRC or CMEC; and a localization signal domain. In some embodiments, the TLR polypeptide is a fusion protein, e.g., includes a send protein, e.g., a fluorescent protein such as Yellow Fluorescent Protein (YFP), Cyan Fluorescent Protein (CFP), Red Fluorescent Protein (RFP), or Green Fluorescent Protein (GFP), or a fluorescent variant thereof.

Localization and translocation can be detected by methods known in the art, e.g., fluorescent microscopy or fractionating the cell and testing the fractions for the presence of TLR9 polypeptide. Aggregation can be detected by methods known in the art, e.g., immunoprecipitation, e.g., using anti-TLR9 antibodies, flow cytometry, or Fluorescence Resonance Energy Transfer (FRET) using polypeptides tagged with different fluorescent tags, e.g., YFP or CFP, or by co-immunoprecipitation using anti-TLR9 antibodies. In some embodiments, the compound or test compound is further tested for the ability to modulate TLR9-mediated signaling.

In some embodiments, the sample includes a cell or a cell extract. In some embodiments, the sample includes a cell-free preparation.

The invention also relates to methods of identifying compounds that modulate TLR9 signalling, by modulating the binding of TLR9 polypeptide and a TLR9 ligand, e.g., a CpG-DNA. The methods include providing a sample including a TLR9 polypeptide, e.g., a full-length TLR9 protein or a fragment thereof that includes a ligand binding domain, e.g., a CXXC motif as described herein; contacting the sample with a TLR9 ligand and a test compound, thereby providing a test sample; incubating the test sample under conditions and for a time sufficient for the TLR9 polypeptide and TLR9 ligand to bind in the absence of the test compound, and detecting binding of the TLR9 ligand to the TLR9 polypeptide. A difference in the amount of binding between the TLR9 and ligand in the test sample, e.g., as compared to a reference sample, indicates that the test compound is a compound that modulates TLR9 signalling.

In some cases, the test compound is a modified CpG-DNA or a structurally similar variant thereof. In some embodiments, the TLR9 polypeptide is labeled. For example, the TLR9 polypeptide can be a fusion protein (chimeric protein) such as a fluorescent fusion protein (e.g., with YFP, CFP, RFP, GFP, or a fluorescent variant thereof). In some embodiments, the sample can include a cell (such as an HEK cell or dendritic cell (DC)), or be a cell-extract or cell-free preparation.

In some embodiments, MyD88 (myeloid differentiation primary response gene 88) localization is also detected. The MyD88 can be a fusion protein such as a fluorescent fusion protein (e.g., YFP). In some embodiments, the methods further include determining whether the test compound modulates TLR9-mediated signaling.

The invention also relates to methods of identifying compounds that affect MyD88 localization. The methods include providing a cell or cells that express a MyD88, e.g., a full-length MyD88 or a fragment of a MyD88, e.g., a fragment that includes a localization signal of MyD88 or a fragment that includes a TLR9 binding region; contacting the cell with a test compound, thereby providing a test sample; incubating the test sample under conditions and for a time sufficient for MyD88 localization to occur in the absence of the test compound; and detecting MyD88 localization in the test sample. A difference in MyD88 localization in the test sample, e.g., as compared to MyD88 localization in a reference sample, indicates that the test compound is a compound that affects MyD88 localization. In some cases, MyD88 localization is detected in the tubular lysosomal compartment (TLC). The rate of MyD88 localization may be affected by the compound and can be assayed, e.g., by determining the localization of MyD88 at multiple time points. In some embodiments, the localization of MyD88 in a lysosomal compartment, e.g., the TLC, is affected by the test compound.

In some embodiments, the MyD88 is labeled, for example, the MyD88 is a fusion protein such as a fluorescent fusion protein (e.g., comprising a YFP polypeptide). The test sample can also include one or both of an inducer of MyD88 or TLR9 signaling, e.g., a CpG-DNA. In one embodiment, the test sample includes a CpG-DNA, and MyD88 localization in the TLC is detected. In some cases, localization is detected using cell fractionation or microscopy-based methods.

In some embodiments, the methods further include determining whether the test compound modulates TLR9-mediated signaling. A test compound that has been screened by a method described herein and determined to modulate TLR9 signaling, can be considered a candidate compound. A candidate compound that has been screened, e.g., in an in vivo model of a disorder, e.g., a disorder associated with TLR9 signalling, e.g., inflammation, autoimmune disorders, and pathogen infection, and determined to have a desirable effect on the disorder, e.g., on one or more symptoms of the disorder, can be considered a candidate therapeutic agent. Candidate therapeutic agents, once screened in a clinical setting, are therapeutic agents. Candidate therapeutic agents and therapeutic agents can be optionally optimized and/or derivatized, and formulated with physiologically acceptable excipients to form pharmaceutical compositions. The invention also relates to compounds that modulate TLR9 signalling, identified by a method described herein, and therapeutic compositions containing the compounds, as well as methods of treating disorders associated with TLR9 signalling by administering the compounds. Methods of preparing and administering such compounds are known in the art.

As used herein, a "TLR9 polypeptide" can include a full-length TLR9 polypeptide or a suitable fragment thereof. In some embodiments, the TLR9 polypeptide is a chimeric protein, e.g., includes a second protein (e.g., a fluorescent polypeptide, a tag, or an Fc region of an antibody) expressed in frame with the TLR9 as a single molecule. In some embodiments, the TLR9 ligand or TLR9 polypeptide can be bound to a solid surface (in one example, the TLR9 ligand is biotinylated and the solid surface comprises avidin, streptavidin, or NeutrAvidin™, a deglycosylated form of avidin). In another embodiment, the TLR9 ligand and/or TLR9 polypeptide is labeled, e.g., with a lanthanide chelate fluorophore, and time-resolved fluorimetry is used to detect the binding. In some embodiments, an antibody that specifically binds to the TLR9 polypeptide is used to detect binding between a TLR9 polypeptide and a TLR9 ligand; for example, an antibody that specifically binds to a chimeric TLR9 protein (e.g., to the non-TLR9 portion of the chimera) can be used to detect binding between the TLR9 polypeptide and TLR9 ligand. The antibody can be labeled, e.g., with a lanthanide chelate fluorophore, and time-resolved fluorimetry is used to detect the binding. The method can also be performed such that the TLR9 polypeptide and TLR9 ligand are in solution. In another embodiment, the TLR9 polypeptide and/or the TLR9 ligand is bound to a collectable substrate, e.g., a bead.

As used herein, a "reference" is a physical control sample or a level based on a control sample, e.g., an electronic sample. In some embodiments, the reference is a control cell in the absence of a test compound. A reference can be a portion of the same cell. One cell or type of cell can be used as both a test cell and a reference cell.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

Other features and advantages of the invention will be apparent from the detailed description, drawings, and from the claims.

DESCRIPTION OF DRAWINGS

The patent or application file contains at least one drawing executed in color. Copies of this patent or patent application publication with color drawing(s) will be provided by the Office upon request and payment of the necessary fee.

FIGS. 3A-D are confocal images of pDCs that were incubated with CpG-DNA (red) and transferrin (green) for five minutes and imaged by confocal microscopy.

FIGS. 3E-H are confocal images of HEK cells expressing FYVE-GFP (which binds to PI3P on early endosomes) and were incubated with CpG-DNA for five minutes.

FIGS. 3I-L are confocal images pDCs stained to detect albumin (green; a marker for caveolae-mediated internalisation) and CpG (red) that were added to the pDCs for five minutes.

FIGS. 3M-P are confocal images of HEK cells expressing TLR9$^{YFP}$ (red) and caveolin-1$^{CFP}$ (green) that were incubated with CpG-DNA (blue) for five minutes and examined by confocal microscopy.

FIGS. 9A-9D are confocal images of stably transfected HEK-TLR9$^{CFP}$ (green), HEK-TLR9$^{YFP}$ (red) and HEK-TLR9$^{CFP}$/TLR9$^{YFP}$ (yellow) cells grown on glass-bottom tissue culture dishes and either left untreated (9A and 9C) or stimulated with CpG-DNA (9B and 9D, 2006 sequence). Living cells were imaged by confocal microscopy and analyzed for the presence of Fluorescence Resonance Energy Transfer (FRET) using a sensitised emission formula. The areas of highest intensity (red) represent FRET that has been induced by endosomal CpG-DNA.

DETAILED DESCRIPTION

It has been found that TRL9 resides in the endoplasmic reticulum (ER) of resting cells, including transfected cell lines, primary dendritic cells (e.g., plasmacytoid dendritic cells, also referred to herein as pDCs), and macrophages, and is transported to a lysosomal compartment upon stimulation of the cell with a molecule that can activate TLR9 signaling such as a CpG-DNA. Furthermore, TLR9 has been found to directly bind to TLR9 signaling molecules, e.g., CpG-DNA. Thus, compounds that modulate these activities of TLR9 can be used to modulate TLR9 signaling and consequences of such signaling. Compounds that increase TLR9 signaling are useful for increasing an immune response, for example during vaccine administration. Compounds that decrease TLR9 signaling are useful for decreasing an immune response, for example, to decrease inflammation.

The expression pattern of TLR9, which localizes to the ER, is in sharp contrast to the expression pattern of other TLRs, such as TLR2 and TLR4, both of which enter the secretory pathway and traffic to the plasma membrane. Also, CpG-DNA, which is involved in the initiation of TLR9-mediated signaling, was found to internalize via a clathrin-dependent endocytic pathway and rapidly moves into a tubular lysosomal compartment (TLC). As described herein, upon CpG-DNA stimulation of dendritic cells (DCs) and macrophages, both TLR9 and MyD88 (myeloid differentiation primary response gene 88) were found to rapidly redistribute toward sites of CpG-DNA accumulation. As CpG-DNA is internalized, TLR9 distribution changes, with a portion of the total pool of protein moving into early endosomes and later into the tubular lysosomal compartment, where TLR9 aggregates. Furthermore, it is demonstrated herein that CpG-DNA directly binds to TLR9. Thus, TLR9 is expressed in the ER and translocates to a CpG-DNA containing lysosomal compartment for ligand binding and signal transduction. Accordingly, the translocation of TLR9 that accompanies CpG-DNA internalization places the receptor (TLR9) in the same cellular compartment as its ligand (CpG-DNA), thereby initiating TLR9-mediated signaling.

Binding assays of CpG-DNA/TLR9 interactions successfully predicted the pharmacological responses of cells to a variety of CpG oligonucleotides, including the ability of non-stimulatory GpC-DNA to interfere with signal transduction induced by CpG-DNA. Further evidence that signal transduction begins in these CpG-rich compartments was the rapid appearance of MyD88, which participates in TLR9-mediated signaling, in the same area.

Figure 6A:
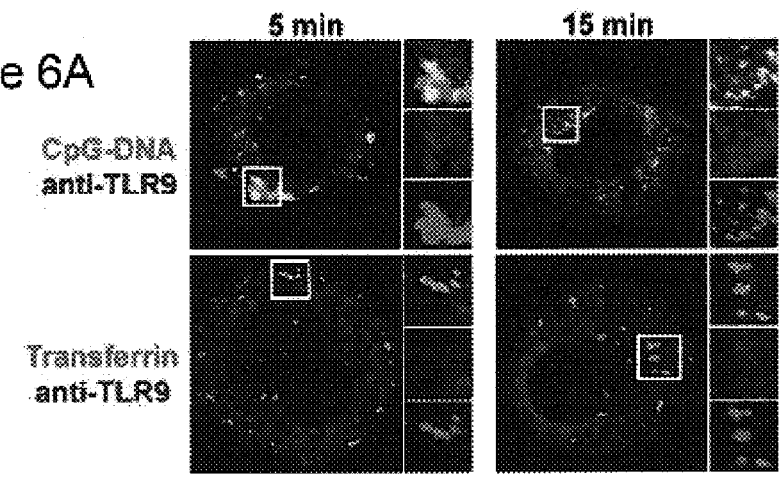
FIG. 6A is a set of confocal images of human pDCs that were incubated with Texas Red-CpG-DNA or Alexa 546-conjugated transferrin for the indicated time periods. After fixation, TLR9 was stained intracellularly by direct immunofluorescence (anti-TLR9).
Figure 6B:
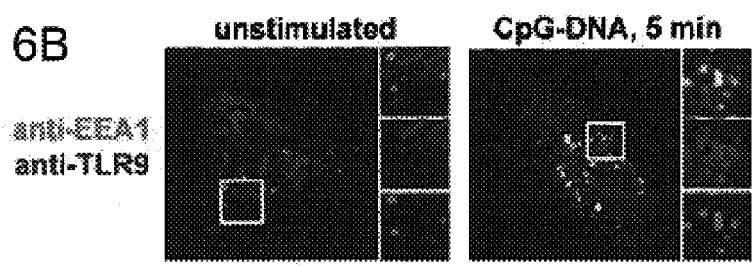
FIG. 6B is a set of confocal images of non-stimulated or CpG-DNA stimulated (five minutes) pDCs that were co-stained with anti-TLR9 and the early endosome marker protein EEA1 (FITC).
Figure 6C:
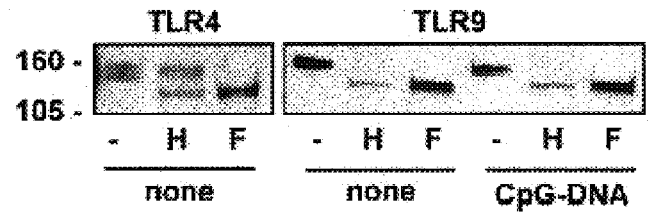
FIG. 6C is a reproduction of Western blots from an experiment in which HEK cells that were stably transfected with TLR9$^{YFP}$ or TLR4$^{YFP}$ were grown in monolayers. Cells were then lysed and immunoprecipitated TLRs (TLR4 or TLR9) were left untreated (−), were treated with endoglycosidase H (H), or were treated with peptide:N-glycosidase F (F). Deglycosylated or untreated TLRs were subjected to SDS-gel electrophoresis and Western blot using anti-GFP to detect the TLRs.

There are several possible ways that proteins can reach lysosomal compartments from the ER. Lysosomes can be accessed via the secretory pathway (Mellman, 1996, Annu. Rev. Cell. Dev. Biol. 12:575-625). In the secretory pathway, proteins traffic via the Golgi to the plasma membrane, where they are internalized and shuttled to their destination due to sequence inherent lysosomal sorting motifs. As described herein, biochemical studies employing endoglycosidases demonstrate that TLR9 does not enter the secretory pathway because TLR9—in both resting and CpG-DNA stimulated cells—never acquires EndoH resistance. Thus, compounds that specifically affect TLR9 localization in response to stimulation of the cell by a CpG-DNA will not affect secretory pathways that can affect other cellular functions. Although it was observed that TLR9 was absent from the plasma membrane, surface biotinylation studies in stimulated TLR9-expressing cells revealed that a small portion of TLR9 becomes surface accessible after CpG-DNA exposure (FIG. 6C).

TLR9 recognizes unmethylated bacterial CpG-DNA, and is a potent inducer of a Th1-type immune response. The observation that the binding of CpG-DNA to TLR9 is sequence independent suggests that although compounds related to CpG-DNA may be inhibitors of TLR9-mediated signal transduction, other potent inhibitors might be identified. Assays described herein can be used to identify such inhibitors. Candidate compounds can, but need not, have CpG-related motifs. Such inhibitors are candidates for treatment of, for example, DNA-related chronic inflammatory diseases such as systemic lupus erythematosus. Molecules that increase the effects of TLR9 (e.g., by facilitating transport of TLR9 to the ER or tubular lysosomal compartment (TLC), facilitating TLR9 aggregation, acting as a TLR9 agonist by binding to TLR9, or enhancing the binding of TLR9 to CpG-DNA), can increase TLR9-mediated signaling. Such compounds are useful for increasing the immune stimulatory effects of TLR9, e.g., to stimulate protective immunity against infectious agents such as anthrax, plague, Ebola, influenza, vaccinia, hepatitis C, and smallpox as well as other disorders such as asthma and allergic rhinitis, and for use in vaccine protocols including anti-cancer vaccines, e.g., as adjuvants. Compounds that increase TLR9-mediated signaling (TLR9 agonists) are also useful for treatment of cancer, either alone or in conjunction with other therapies; TLR9 signaling is essential in mediating the anti-inflammatory effect of probiotics (Rachmilewitz et al., Gastroenterology, 2004, 126(2):520-8). Compounds that inhibit TLR9 signalling are useful in the treatment of disorders associated with increased TLR9 signalling, e.g., disorders associated with an overactive Th1-type immune response, e.g., inflammatory and autoimmune responses, e.g., in lupus nephritis (Anders et al., FASEB J., 2004, 18(3):534-6).

Screening Assays

The new methods (also referred to herein as "screening assays") can be used to identify modulators of TLR9 signalling, i.e., candidate compounds or agents (e.g., proteins, peptides, peptidomimetics, peptoids, small inorganic molecules, small non-nucleic acid organic molecules, nucleic acids (e.g., anti-sense nucleic acids, siRNA, oligonucleotides, synthetic oligonucleotides, or other drugs) that have at least one of the following properties: affect binding of TLR9 and a cognate ligand, bind to TLR9 or TLR9-associated proteins, have a stimulatory or inhibitory effect on, for example, TLR9 activity (e.g., by affecting TLR9 localization or aggregation), or have a stimulatory or inhibitory effect on, for example, the activity of TLR9-mediated downstream signaling pathway components. Compounds thus identified can be used to modulate the activity of TLR9 (e.g., TLR9-mediated signaling or MyD88-mediated signaling) in a therapeutic protocol or to elaborate the biological function of TLR9 or MyD88. In all of the assays described herein, a full-length TLR9 can be used or a fragment of TLR9 that has the required activity can be used. The TLR9 (full-length or fragment) can be a hybrid protein that includes a detectable reporter molecule such as a fluorescent protein.

In the assays described herein, any method known in the art can be used to stimulate TLR9 signaling, e.g., stimulation with CpG-DNA. The concentration of the inducing agent (e.g., CpG-DNA) should be sufficient to induce translocation in the absence of the test compound (e.g., for CpG-DNA a concentration of about 0.1-10 µM).

Assays are provided herein for screening test compounds that can affect the localization of TLR9 or MyD88. In another embodiment, assays are provided for screening test compounds that bind to TLR9. In other embodiments, assays are provided for screening test compounds that can affect the aggregation of TLR9, i.e., the formation of TLR9 multimers (e.g., dimers, trimers, or higher-order multimers). Assays for identifying compounds that modulate an additional activity (for example, activity associated with TLR9-mediated signaling) of a TLR9 or MyD88 polypeptide (e.g., a full-length protein or a biologically active portion thereof) are also included. In general, test compounds that affect TLR9 localization are termed "candidate" compounds for modulating TLR9 localization, trafficking behavior, or activity, and are useful for modulating TLR9-mediated effects. For example, such compounds are useful for modulating a TLR9-mediated immune response or inflammation. In addition, compounds previously identified as modulators of TLR9-mediated signaling can be tested for their ability to affect TLR9 localization. Such assays can serve to elucidate the mechanism of action of these compounds. Generally, it is desirable that compounds used for these purposes be as specific in their action as possible. For example, it is desirable, although not required, that a compound modulate TLR9 localization, but not the localization of other proteins.

Compounds identified as candidate compounds that modulate TLR9 localization, trafficking behavior, or activity, and are useful for modulating TLR9-mediated effects can be considered candidate therapeutic compounds for the treatment of disorders associated with TLR9 signaling, e.g., the immune response to pathogens, e.g., anthrax, plague, Ebola, influenza, vaccinia, hepatitis C, and smallpox as well as other disorders such as asthma and allergic rhinitis, and for use in vaccine protocols including anti-cancer vaccines. Compounds that increase TLR9-mediated signaling (TLR9 agonists) are also useful for treatment of cancer, either alone or in conjunction with other therapies. A candidate therapeutic compound that has been screened, e.g., in an in vivo model of a disorder associated with TLR9 signaling, and determined to have a desirable effect on the disorder, e.g., on one or more symptoms of the disorder, can be considered a candidate therapeutic agent. Candidate therapeutic agents, once screened in a clinical setting, are therapeutic agents. Candidate therapeutic agents and therapeutic agents can be optionally optimized and/or derivatized using methods known in the art, and formulated with physiologically acceptable excipients to form pharmaceutical compositions.

In general, localization and aggregation assays are performed using test cells that either express an endogenous TLR9 or have been genetically engineered to express TLR9, e.g., a fluorescent TLR9 fusion protein, either stably or transiently. The cells are cultured under conditions in which the TLR9 is expressed, and, in some embodiments, in the presence of a TLR9 stimulator such as CpG DNA and/or a test compound. After incubating the cells under conditions and for a time sufficient for the test compound to affect TLR9 localization (at least about 1 minute, e.g., about 5 minutes, 10 minutes, 15 minutes, 30 minutes, 1 hour, 3 hours, 6 hours, 8 hours, 16 hours, or 24 hours) the cells are examined for the location and/or aggregation of TLR9. In some cases, the rate of localization of TLR9 is assayed. Optionally, the localization of other molecules, e.g., MyD88, CpG DNA, and/or the test compound can be examined. A difference in the localization of TLR9 in the presence of the stimulator and/or test compound, as compared to localization of TLR9 in a reference, e.g., a control cell in the absence of the test compound, indicates that the test compound can affect TLR9 localization. The difference can be, e.g., a subjective or objective measure of the amount of TLR9 in a subcellular compartment compared to a reference, or a ratio of the amount of TLR9 in a selected subcellular compartment compared to a reference portion of the same cell. One cell or type of cell can be used as both a test cell and a reference cell.

If the compound causes a decreased amount of TLR9 in a subcellular compartment when compared to a reference, the total amount of TLR9 polypeptide and/or nucleic acid can be considered. Thus, a compound that decreases the total amount of TLR9 in a cell is also a candidate compound for modulating TLR9 expression or activity. In general, a compound that decreases (e.g., compared to a reference that did not contain the test compound) the amount of TLR9 in the ER (in the absence of stimulation of TLR9-mediated signaling) or, after induction of the cell with an inducer (e.g., a CpG-DNA), decreases the amount of TLR9 in the TLC or the rate of localization of TLR9 to a lysosomal compartment (e.g., the tubular lysosomal compartment (TLC)), is a compound that decreases the expression or activity of TLR9. A compound that disrupts the localization of TLR9 to the ER or the TLC (e.g., after incubating the cell in the presence of a CpG-DNA) is also a candidate compound for decreasing the expression or activity of TLR9. If an increased rate of localization of TLR9 to the ER, an increased steady state amount of TLR9 in the ER, or, upon incubation in the presence of a CpG-DNA, an increased amount of TLR9 in the tubular lysosomal compartment or an increased rate of localization to the TLC are observed in the presence of the test compound, the test compound is a candidate compound for increasing TLR9 expression or activity.

Localization of TLR9 or MyD88

Localization of TLR9 polypeptide, and/or the rate of localization of TLR9 polypeptide, can be determined using methods known in the art and methods described herein. Suitable methods include microscopic evaluation of tagged polypeptides, e.g., fluorescent tagged polypeptides, and cell fractionation methods.

Green fluorescent protein (GFP) is a fluorescent molecule that was cloned from the jellyfish *Aequorea victoria*. Several genetic modifications of GFP have led to variants, such as 'enhanced green fluorescent protein' (referred to as eGFP), that have enhanced fluorescence characteristics. Additional spectral variants of GFP with color shifts into the yellow and blue regions of the visible spectrum have also been identified. Fluorescent variants of GFP, such as enhanced yellow, red, and cyan fluorescent protein (YFP, RFP, and CFP), are optimal for dual labeling in living cells, because they exhibit distinct spectral peaks for excitation and emission. In addition, CFP and YFP have fluorescence characteristics that allow their application in FRET experiments.

As one example, photoactivatable fusion proteins that include a TLR9 polypeptide (full-length TLR9 or a fragment thereof) can be used to track TLR9 localization and determine the rate of localization (e.g., in the presence and absence of a TLR9 stimulator and/or test compound). Such assays can be carried out, e.g., by expressing paGFP (photoactivatable GFP), which is a mutant GFP, in a cell. paGFP exhibits extremely low fluorescence when excited at 488 nm, which is the optimal wavelength for excitation of GFP (Patterson et al., 2002, Science, 297:1873-1877). At 488 nm, the fluorescence of GFP is about 100 times that of paGFP. paGFP is optimally excited at 405 nm, and at this wavelength, fluorescence of paGFP is increased about 100 times. The nucleic acid sequence encoding paGFP is fused to a TLR9 polypeptide-coding sequence. Expression of the fusion protein in, e.g., HEK cells, permits excitation of the TLR9-paGFP in a small selected region of the cell by exposing the selected region to light at 405 nm. Thus, only the TLR9-paGFP that was in the selected region is fluorescent. The excited molecules from that region can then be tracked in the cells. For example, the progress of the TLR9-paGFP molecules that were excited by illumination can be detected over time either with or without exposure of the cell to agonist. Addition of a test compound to the cell expressing the TLR9-paGFP, excitation of a selected region, and detection of the rate of transit of the excited TLR9-paGFP can therefore be used as an assay for the ability of a test compound to modulate localization and/or the rate of localization of TLR9.

Aggregation of TLR9

A number of assays are known in the art and provided herein for screening test compounds that can affect the aggregation of TLR9, including immunoprecipitation (see, e.g., Harlow and Lane, *Antibodies: A Laboratory Manual* Cold Spring Harbor Laboratory Press (New York, 1988)), flow cytometry (see, e.g., Chan et al., 2004, Methods Mol Biol., 261:371-82), and fluorescence microscopy-based methodologies (see, e.g., Bunt and Wouter, 2004, Int. Rev. Cytol., 237:205-77).

For example, one way to test the induction of ligand induced changes of the subcellular localization or changes of the aggregation state of a receptor is to utilize Fluorescence Resonance Energy Transfer (FRET) (see, for example, Lakowicz et al., U.S. Pat. No. 5,631,169; Stavrianopoulos, et al., U.S. Pat. No. 4,868,103). FRET is an alternative and complementary approach to traditional methods to identify molecular interaction, based on fluorescence technology. The basic principle of FRET relies on a distance-dependent interaction between the excited states of two dye molecules in which excitation is transferred from a donor molecule (e.g., a fluorescent moiety such as CFP) to an acceptor molecule (e.g., a different fluorescent moiety such as YFP) in a non-radiative fashion. A fluorophore label on a first, 'donor' molecule is selected such that its emitted fluorescent energy will be absorbed by a fluorescent label on a second, 'acceptor' molecule, which in turn is able to fluoresce due to the absorbed energy.

Alternately, the 'donor' protein molecule may simply utilize the natural fluorescent energy of tryptophan residues. Labels are chosen that emit different wavelengths of light, such that the 'acceptor' molecule label may be differentiated from that of the 'donor.' Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. A FRET binding event can be conveniently measured through standard fluorometric detection means well known in the art (e.g., using a fluorimeter). FRET is dependent on the inverse sixth power of the intermolecular separation and is operative over distances comparable to the dimensions of biological macromolecules.

Fluorescence microscopy with currently-available hardware and software can achieve spatial resolution close to the theoretical limits of optical resolution between 200 and 300 nm. FRET occurs if the acceptor is within a radial distance of less than 10 nm (100 Angstrom) from the donor. Thus, FRET imaging increases the resolution of microscopic imaging to the order of 1-10 nm. The main advantage of the use of FRET imaging is that this method can be performed in living cells. One of the important conditions for FRET is the overlap of the emission spectrum of a donor molecule with the absorption spectrum of an acceptor. As a result of this spectral overlap, the FRET signal is always contaminated by donor emission (spectral bleedthrough) into the acceptor channel and by excitation of the acceptor molecule by the donor excitation wavelength (crossexcitation). Mathematical algorithms are required to correct for the spectral bleedthrough and crossexcitation (see, e.g., Example 6).

FIG. 9 illustrates that the addition of CpG-DNA also leads to TLR9 aggregation within the endosomal compartment. Thus, FRET can be used as a screenable endpoint for the activation of TLR9.

A complementary method for measuring molecular interaction is a time-resolved fluorescence microscopic method that is referred to as Fluorescence Lifetime Imaging (FLIM) (see, e.g., Lakowicz et al., 1992, Proc Natl Acad Sci U.S.A., 89(4):1271-5, and Lakowicz et al., 1992, Anal Biochem., 202(2):316-30). The fluorescence lifetime is defined as the average time that a molecule remains in an excited state prior to returning to the ground state. To measure the lifetime of a given fluorophore, the sample is excited with a pulsed laser source at a certain frequency. In between the laser pulses, the fluorescence decay times are recorded by a sensitive photomultiplier, and the individual fluorochromes can be identified by their differences in fluorescence lifetime. The lifetime of a fluorophore is independent of spectral bleed-through or fluorophore concentration but highly dependent on the local environment of the fluorophore, such as the occurrence of energy transfer (FRET). The presence of acceptor molecules in close proximity to donor molecules will influence the fluorescence lifetime of the donor. The combination of FRET and FLIM provides a high spatial (nanometer) and temporal (nanosecond) resolution when compared to intensity based FRET imaging.

Modulation of TLR9 Activity

In some cases, the methods described herein include another type of cell-based assay, e.g., an assay in which a cell that expresses a TLR9 protein or biologically active portion thereof is contacted with a test compound, and the ability of the test compound to modulate TLR9 activity is determined. Additional assays for increased or decreased expression or activity of TLR9 can be performed contemporaneously with, before, or after performing an assay described herein, e.g., a binding localization or aggregation assay. Such additional assays can be used to further test the suitability of a compound for use as a modulator of TLR9 activity. Methods of assaying TLR9 expression include methods that assay RNA levels (e.g., Northern blot analysis or quantitative PCR) and methods that assay protein levels (e.g., quantitative immunoassay methods). The ability of the test compound to modulate TLR9 activity can be determined using, e.g., an assay of TLR9 mediated signaling as described herein or known in the art. The cell, for example, can be of mammalian origin, e.g., murine or human. The TLR9 can, in vivo, interact with one of more cellular or extracellular macromolecules such as a MyD88 or CpG DNA. For purposes of this application, such cellular and extracellular macromolecules are referred to herein as "binding partners." Compounds that disrupt such interactions can be useful in regulating the activity of the TLR9. Such compounds can include, but are not limited to, molecules such as antibodies, peptides, and small molecules as described herein. In an alternative embodiment, methods are provided for determining the ability of the test compound to modulate the activity of a TLR9 protein through modulation of the activity of a downstream effector of a TLR9 target molecule. For example, the activity of the effector molecule on an appropriate target can be determined, or the binding of the effector to an appropriate target can be determined, as described herein.

CpG-DNAs

CpG-DNAs include the unmethylated sequence GTCGTT, which is generally used when the assay includes a human TLR9, and GACGTT, which is generally used when the TLR9 is murine. Other CpG-DNAs can be used. CpG-DNAs may have multiple CpG motifs in a single molecule (e.g., CpG-containing oligonucleotide). Methods of identifying CpG-DNAs are known in the art, for example, see Krug et al. (2001, Eur. J. Immunol., 31:2154-2163) and Bauer et al. (2001, Proc. Nat. Acad. Sci. U.S.A., 98:9237-9242); Kandimalla et al. (2003, Proc. Nat. Acad. Sci. U.S.A., 100:14303-14308); Agrawal et al. (2002, Trends Mol. Med., 8:114-121). In some embodiments, a reference CpG-DNA is used. CpG-DNAs and reference CpG-DNAs can be synthesized using methods known in the art or obtained from commercial sources (e.g., InvivoGen, San Diego, Calif.; MWG-Biotech, High Point, N.C.; Invitrogen, Carlsbad, Calif.).

In some methods, a reference CpG-DNA is used that does not stimulate TLR9 signaling. An example of such a molecule is a CpG-DNA that has been methylated, or the non-stimulatory GpC-DNA (an inactive oligonucleotide with a reversed CpG motif). Additional CpG-DNA-related compounds that can be used in the methods described herein, e.g., as test compounds are discussed infra.

TLR9 Polypeptides

In general, any known TLR9 protein can be used in the methods described herein. TLR9 is described in the Online Mendelian Inheritance in Man database (OMIM; available at www.ncbi.nlm.nih.gov/entrez/query.fcgi?db=OMIM) at Accession no. *605474, and in the UniGene database (available at www.ncbi.nlm.nih.gov/entrez/query.fcgi?db=unigene) at UniGene Cluster Hs.87968 (*Homo sapiens*), Mm.44889 (*Mus musculus*), and Rn.92495 (*Rattus norvegicus*). Nucleic acid sequences encoding a TLR9 can be used, e.g., in expression vectors to produce ectopic expression of the TLR9 (or TLR9 fragment). TLR9 sequences useful in the methods described herein include those of GenBank accession nos. BC032713.1 (*homo sapiens*) (SEQ ID NO:1), NM_031178.1 (*mus musculus*) (SEQ ID NO:2), and NM_198131.1 (*rattus norvegicus*) (SEQ ID NO:3). The sequences referenced by these GenBank numbers are incorporated herein by reference. Exemplary sequences are illustrated below.

Suitable fragments of a TLR9 protein can also be used in assays. For example, a CpG-DNA binding region of TLR9, the region of TLR9 that contains the ER localization signal sequence or the lysosomal localization signal sequence.

The general architecture of TLR9 includes an N-terminal region (sometimes referred to as the "extracellular" domain or ECD), which includes two leucine-rich repeat (LRR) regions, e.g., amino acids 64-435 (LRR region 1) and 473-750 (LRR region 2) of SEQ ID NO:1; a single transmembrane domain, e.g., amino acids 819-839 of SEQ ID NO:1; and then the TIR domain (Toll/IL-1 Resistance signaling domain) at the C-terminus, e.g., amino acids 868-1016 of SEQ ID NO:1 (Akira, Curr. Opin. Immunol. 15:5-11 (2003)). TLR9 also contains a signal sequence, e.g., amino acids 1-25 of SEQ ID NO:1. In general, regions of a TLR9 containing a CXXC motif, e.g., CRRC at amino acids 255-258 of SEQ ID NO:1 or CMEC at amino acids 265-268 of SEQ ID NO:1, are potential nucleic acid ligand binding domains, e.g., for CpG-DNA. For assays that involve ligand binding, the fragment typically contains at least one binding domain (e.g., the "extracellular" domain of TLR9 (which is located on the outside of endosomes or outside the lumen of the ER), including one or more LRR regions, e.g., at least LRR1) or in assays that detect localization, at least a localization signal domain, e.g., amino acids 888-902 and/or 928 and 1013 of SEQ ID NO:1. For assays of aggregation, the fragment can include, e.g., the extracellular domain, e.g., the leucine-rich regions (LRR regions 1 and 2), and/or the intracellular TIR domain. Similarly, for assays involving MyD88, the entire protein or a fragment having the required activity (e.g., the MyD88 localization sequence, or TLR9-binding fragments) can be used. Such regions can be determined using methods known in the art and used in binding studies.

Variants of TLR9 can also be used. Variants will be at least 80%, e.g., 85%, 90%, or 95% identical to the full length of a TLR9 sequence described herein e.g., SEQ ID NO:1, 2, or 3, as determined using the Needleman and Wunsch (1970, J. Mol. Biol. 48:444-453) algorithm, (which has been incorporated into the GAP program in the GCG software package available on the world wide web at www.gcg.com), using a Blossum 62 scoring matrix with a gap penalty of 12, a gap extend penalty of 4, and a frameshift gap penalty of 5. Suitable full-length variants can activate NFκB in a cellular activation assay, e.g., as described herein. Fragments of the variants can also be used.

TLR9 polypeptides also include TLR9 fusion proteins. Methods of engineering a TLR9 fusion protein (e.g., with a tag such as a fluorescent protein, or with the Fc region of an antibody) suitable for use in the assays are within the scope of the art (e.g., Latz et al., 2002, supra). As described herein, TLR9-fluorescent protein fusion proteins can be engineered to enable tracking the TLR9 polypeptide by virtue of the molecular tag in a variety of experimental systems. TLR9:Fc fusion proteins can also be used, e.g., as described in U.S. Provisional Patent Application Ser. No. 60/598,774, filed Aug. 4, 2004, the disclosure of which is incorporated by reference herein. Stable cell lines have been established using such methods (e.g., Latz et al., 2002, supra). The stable cell lines have the common characteristic of stably expressing a chimeric fluorescent TLR. In general, the chimeric fluorescent TLR can, upon stimulation of the cell by a molecule known to activate the signaling pathway of the naturally occurring cognate of the chimeric TLR, induce one or more activities of the signaling pathway.

Exemplary TLR9 Protein Sequences:

BC032713.1 (homo sapiens):

(SEQ ID NO:1)

```
  1 mgfcrsalhp lsllvqaiml amtlalgtlp aflpcelqph glvncnwlfl ksvphfsmaa
 61 prgnvtslsl ssnrihhlhd sdfahlpslr hlnlkwncpp vglspmhfpc hmtiepstfl
121 avptleelnl synnimtvpa lpkslislsl shtnilmlds aslaglhalr flfmdgncyy
181 knpcrqalev apgallglgn lthlslkynn ltvvprnlps sleylilsyn rivklapedl
241 anltalrvld vggncrrcdh apnpcmecpr hfpqlhpdtf shlsrleglv lkdsslswln
301 aswfrglgnl rvldlsenfl ykcitktkaf qgltqlrkln lsfnyqkrvs fahlslapsf
361 gslvalkeld mhgiffrsld ettirplarl pmlqtlrlqm nfinqaqlgi frafpglryv
421 dlsdnrisga seltatmgea dggekvwlqp gdlapapvdt pssedfrpnc stlnftldls
481 rnnlvtvqpe mfaqlshlqc lrlshncisq avngsqflpl tglqvldlsh nkldlyhehs
541 ftelprleal dlsynsqpfg mqgvghnfsf vahirtirhi slahnnihsq vsqqlcstsl
601 raldfsgnal ghmwaegdly lhffqglsgl iwldlsqnrl htllpqtlrn lpkslqvlrl
661 rdnylaffkw wslhflpkle vldlagnqlk altngslpag trlrrldvsc nsisfvapgf
721 fskakelrel nlsanalktv dhswfgplas alqildvsan plhcacgaaf mdfllevqaa
781 vpglpsrvkc gspgqlqgls ifaqdlrlcl dealswdcfa isliavalgi gvpmlhhlcg
841 wdlwycfhlc lawlpwrgrq sgrdedalpy dafvvfdktq savadwvyne lrgqleecrg
901 rwalrlclee rdwlpgktlf enlwasvygs rktlfvlaht drvsgllras fllaqqrlle
```

-continued
```
 961 drkdvvvlvi  lspdgrrsry  vrlrqrlcrq  svllwphqps  gqrsfwaqlg  maltrdnhhf
1021 ynrnfcqgpt  ae
```

NM_031178.1 (mus musculus)

(SEQ ID NO:2)
```
   1 mvlrrrtlhp  lsllvqaavl  aetlalgtlp  aflpcelkph  glvdcnwlfl  ksvprfsaaa
  61 scsnitrlsl  isnrihhlhn  sdfvhlsnlr  qlnlkwncpp  tglsplhfsc  hmtieprtfl
 121 amrtleelnl  syngittvpr  lpsslvnlsl  shtnilvlda  nslaglyslr  vlfmdgncyy
 181 knpctgavkv  tpgallglsn  lthlslkynn  ltkvprqlpp  sleyllvsyn  livklgpedl
 241 anltslrvld  vggncrrcdh  apnpciecgq  kslhlhpetf  hhlshleglv  lkdsslhtln
 301 sswfqglvnl  svldlsenfl  yesinhtnaf  qnltrlrkln  lsfnyrkkvs  farlhlassf
 361 knlvslqeln  mngiffrsln  kytlrwladl  pklhtlhlqm  nfinqaqlsi  fgtfralrfv
 421 dlsdnrisgp  stlseatpee  addaeqeell  sadphpapls  tpasknfmdr  cknfkftmdl
 481 srnnlvtikp  emfvnlsrlq  clslshnsia  qavngsqflp  ltnlqvldls  hnkldlyhwk
 541 sfselpqlqa  ldlsynsqpf  smkgighnfs  fvthlsmlqs  lslahndiht  rvsshlnsns
 601 vrfldfsgng  mgrmwdeggl  ylhffqglsg  llkldlsqnn  lhilrpqnld  nlpkslklls
 661 lrdnylsffn  wtslsflpnl  evldlagnql  kaltngtlpn  gtllqkldvs  snsivsvvpa
 721 ffalavelke  vnlshnilkt  vdrswfgpiv  mnltvldvrs  nplhcacgaa  fvdlllevqt
 781 kvpglangvk  cgspgqlqgr  sifaqdlrlc  ldevlswdcf  glsllavavg  mvvpilhhlc
 841 gwdvwycfhl  clawipilar  srrsaqtlpy  dafvvfdkaq  savadwvyne  lrvrleerrg
 901 rralrlcled  rdwlpgqtlf  eniwaslygs  rktlfvlaht  drvsgllrts  fllaqqrlle
 961 drkdvvvlvi  lrpdahrsry  vrlrqrlcrq  svlfwpqqpn  gqggfwaqls  taltrdnrhf
1021 ynqnfcrgpt  ae
```

NM_198131.1 (rattus norvegocus)

(SEQ ID NO:3)
```
   1 mvlcsrtlhp  lsllvqaavl  aealalgtlp  aflpcelkph  glvdcnwlfl  ksvphfsaae
  61 prsnitslsl  ianrihhlhn  ldfvhlpnvr  qlnlkwncpp  pglsplhfsc  rmtiepktfl
 121 amrmleelnl  syngittvpr  lpssltnlsl  shtnilvlda  sslaglhslr  vlfmdgncyy
 181 knpcngavnv  tpdaflglsn  lthlslkynn  ltevprqlpp  sleylllsyn  livklgpedl
 241 anltslrvld  vggncrrcdh  apdlctecrq  ksldlhpqtf  hhlshleglv  lkdsslhsln
 301 skwfqglvnl  svldlsenfl  yesinktsaf  qnltrlrkld  lsfnyckkvs  farlhlassf
 361 kslvslqeln  mngiffrlln  kntlrwlagl  pklhtlhlqm  nfinqaqlsv  fstfralrfv
 421 dlsnnrisgp  ptlsrvapek  adeaekgvpw  pasltpalps  tpvsknfmvr  cknlrftmdl
 481 srnnlvtikp  emfvnlshlq  clslshncia  qavngsqflp  ltnlkvldls  ynkldlyhsk
 541 sfselpqlqa  ldlsynsqpf  smqgighnfs  flanlsrlqn  lslahndihs  rvssrlysts
 601 veyldfsgng  vgrmwdeedl  ylyffqdlrs  lihldlsqnk  lhilrpqnln  ylpksltkls
 661 frdnhlsffn  wsslaflpnl  rdldlagnll  kaltngtlpn  gtllqkldvs  snsivfvvpa
 721 ffalavelke  vnlshnilkt  vdrswfgpiv  mnltvldvss  nplhcacgap  fvdlllevqt
 781 kvpglangvk  cgsprqlqgr  sifaqdlrlc  lddvlsrdcf  glsllavavg  tvlpllqhlc
 841 gwdvwycfhl  clawlplltr  grrsaqalpy  dafvvfdkaq  savadwvyne  lrvrleerrg
 901 rralrlcled  rdwlpgqtlf  eniwaslygs  rktlfvlaht  dkvsgllrts  fllaqqrlle
 961 drkdvvvlvi  lrpdahrsry  vrlrqrlcrq  svlfwphqpn  gqgsfwaqls  taltrdnhhf
1021 ynrnfcrgpt  ae
```

Cell Lines

Any type of cell that can express and transport TLR9 as described herein (e.g., to the ER, and upon contacting the cell with CpG-DNA, translocation to the TLC or a vesicular lysosomal compartment) can be used in the assays. In general, suitable cell types include cells of the immune system such as dendritic cells (e.g., primary dendritic cells), B cells, B cell-like cell lines, macrophages, macrophage-like cell lines (e.g., the murine RAW cell line), natural killer cells (NK cells), and cultured cells.

Detection Methods

TLR9 can be visualized using any of a number of methods known in the art. For example, a TLR9 fusion protein that includes at least the portion of TLR9 that is sufficient for correct translocation to the ER, and generally, for correct localization to the TLC upon induction. The fusion protein generally includes a detectable marker polypeptide portion such as a fluorescent protein (e.g., YFP, GFP, RFP, or CFP) or an antigenic polypeptide that can be detected using an antibody (e.g., FLAG-tag, HIS-tag, or V5-tag). In some cases, direct detection of TLR9 or a portion thereof can be performed, using, e.g., an antibody that specifically binds to TLR9 or a suitable fragment thereof. Such antibodies are described in the art and can be obtained from commercial sources (e.g., eBiosciences, San Diego, Calif.).

In some cases, the localization of TLR9 in the presence and absence of the test compound is detected in a cell that has been fixed. Standard methods of fixation can be used. These methods generally preserve ER, TLC, and vesicular lysosomal structures and do not destroy the antigenic portion of the detected molecule if an immunocytochemical method of detection is used. Alternatively, the rate or type of localization can be detected using vital techniques such as confocal microscopy. In the latter case, a fluorescent fusion protein including TLR9 or a biologically active portion thereof is detected.

In some cases, the rate or type of TLR9 localization in the presence of a test compound is determined. This method is generally used to detect translocation of TLR9 to the TLC upon stimulation with a TLR9 agonist such as CpG-DNA in the presence of a test compound. Cells are sampled at various times and an amount of TLR9 present in a subcellular compartment is determined. A second, reference protein can also be monitored (as in all assays provided herein) to provide a normalization reference. A reference protein is typically one whose amount of expression and localization are unaffected by activation of TLR9-mediated signaling. In general, ER-resident proteins (e.g., calnexin or calreticulin) or fluorescent hybrids thereof can be used. In some assays, a cell sample expressing a TLR9 can be contacted with a test compound and at various time intervals, a portion of the cell sample is lysed and fractionated using methods known in the art. In this method, the accumulation of TLR9 in the ER is generally assayed. If the assay is being performed in the presence of an inducer (e.g., CpG-DNA) the accumulation of TLR9 in the tubular lysosomal fraction is generally assayed. Lysosomal markers such as LAMP-1 (lysosomal associated membrane protein) can be used to detect the lysosomal fraction (e.g., using antibodies that detect LAMP-1 or dansylated LAMP-1).

In some embodiments, MyD88 (myeloid differentiation primary response gene 88) localization is assayed. MyD88 is a cytoplasmic adaptor protein with a TIR domain similar to that of TLRs in the C-terminal domain. The protein is required for TLR signaling. In such assays, the localization of MyD88 to the TLC upon induction (e.g., with CpG-DNA) is detected. The methods described above for TLR9 assays can be employed. In addition, both MyD88 and TLR9 localization can be assayed. If desired, MyD88 localization can be measured in the same sample as TLR9, as long as the two molecules carry different labels or can be distinguished by antibodies used for detection. Generally, a test compound that decreases the localization of MyD88 to the TLC upon induction with, e.g., CpG-DNA, is a candidate compound for modulating TLR9-mediated signaling and is a candidate compound for modulating a TLR9-mediated response such as an immune response or inflammation.

Binding Assays

It was found that TLR9 directly binds to CpG-DNA. Accordingly, the ability of the test compound to modulate TLR9 binding to a ligand, e.g., a CpG-DNA, can also be evaluated. In general, such assays are performed in an assay mixture that contains a TLR9, a TLR9 ligand, and a test compound. The ability of the test compound to modulate (increase or decrease) binding between the TLR9 and its ligand is evaluated. Ligands are generally TLR9 agonists, and include naturally occurring ligands (such as short bacterial DNAs) and CpG-DNAs. In one embodiment, the ligand is coupled with a radioisotope, fluorescent entity, antigenic entity, or enzymatic label, such that binding of the ligand to TLR9 can be determined by detecting the labeled ligand in a complex. Alternatively, TLR9 can be coupled with a radioisotope or enzymatic label to monitor the ability of a test compound to modulate TLR9 binding to a substrate in a complex. For example, the label can be $^{125}I$, $^{35}S$, $^{14}C$, or $^{3}H$, and the labeled entity be labeled either directly or indirectly, and the radioisotope detected by direct counting of radioemission or by scintillation counting. Alternatively, the label can be enzymatic, for example, horseradish peroxidase, alkaline phosphatase, or luciferase, and the enzymatic label detected by determination of conversion of an appropriate substrate to product. In other embodiments, one of the assay components (the TLR9 or TLR9 ligand) can be labeled with a fluorescent protein (e.g., a hybrid protein or covalently linked fluorescent protein). FRET can also be used. In the binding assays described herein, the TLR9 can be a full-length polypeptide or a fragment thereof that contains at least the ligand binding domain.

In some cases, an assay is performed in which the assay mixture contains essentially only a TLR9 and a test compound, and suitable buffers. In such an assay the ability of the test compound to bind to the TLR9 is evaluated. The test compound and/or the TLR9 can be labeled. Such assays are useful, for example, for identifying the mechanism of action of a compound that affects TLR9-mediated signaling in a cell. The binding assay can serve as an additional assay to determine the mechanism of action of a compound that affects TLR9-mediated localization or signaling. Compounds identified in this type of binding assay can also be used in binding assays testing the ability of a compound identified as capable of binding to TLR9 to interfere with the binding of TLR9 to a TLR9 ligand such as a CpG-DNA.

The ability of a test compound to interact with TLR9 with or without the labeling of any of the interactants can be evaluated. For example, a microphysiometer can be used to detect the interaction of a compound with a TLR9 without the labeling of either the compound or the TLR9 (McConnell et al., 1992, Science 257:1906-1912). As used herein, a "microphysiometer" (e.g., Cytosensor) is an analytical instrument that measures the rate at which a cell acidifies its environment using a light-addressable potentiometric sensor (LAPS). Changes in the acidification rate can be used as an indicator of the interaction between a compound and TLR9.

In yet another embodiment, a cell-free assay is provided in which a TLR9 protein or suitable fragment thereof is contacted with a test compound and the ability of the test compound to bind to the TLR9 protein or biologically active portion thereof is evaluated. In general, fragments of the TLR9 proteins to be used in the methods described herein include fragments that participate in interactions with other TLR9 or non-TLR9 molecules, e.g., fragments with high surface probability scores, and/or fragments comprising the LRR or TIR domains.

Soluble and/or membrane-bound forms of isolated proteins (e.g., TLR9 proteins or suitable fragments thereof) can be used in the cell-free assays of the methods. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

Cell-free assays typically involve preparing a reaction mixture of the TLR9 polypeptide (e.g., a full-length TLR9 or a fragment thereof, e.g., a fragment that contains at least the CpG-binding region) and the test compound under conditions and for a time sufficient to allow the two components to interact and bind, thus forming a complex that can be removed and/or detected.

In another embodiment, determining the ability of the TLR9 protein to bind to a molecule can be accomplished using real-time Biomolecular Interaction Analysis (BIA) (see, e.g., Sjolander et al., 1991, Anal. Chem. 63:2338-2345 and Szabo et al., 1995, Curr. Opin. Struct. Biol. 5:699-705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal that can be used as an indication of real-time reactions between biological molecules.

In one embodiment, the TLR9 or the test substance is anchored onto a solid phase. The TLR9/test compound complexes anchored on the solid phase can be detected at the end of the reaction. In one embodiment, the TLR9 can be anchored onto a solid surface, and the test compound, (which is not anchored), can be labeled, either directly or indirectly, with detectable labels discussed herein.

It may be desirable to immobilize either TLR9, an anti-TLR9 antibody or a test compound to facilitate separation of complexed from uncomplexed forms of one or both of the proteins, as well as to accommodate automation of the assay. Binding of a test compound to a TLR9 protein, or interaction of a TLR9 protein with a TLR9 ligand (such as a CpG-DNA) in the presence and absence of a candidate compound, can be accomplished in any vessel suitable for containing the reactants. Examples of such vessels include microtiter plates, test tubes, and micro-centrifuge tubes. In one embodiment, a fusion protein can be provided that adds a domain that allows a protein (e.g., the TLR9) to be bound to a matrix. For example, glutathione-S-transferase/TLR9 fusion proteins or glutathione-S-transferase/target fusion proteins can be adsorbed onto glutathione Sepharose™ beads (Sigma Chemical, St. Louis, Mo.) or glutathione derivatized microtiter plates, which are then combined with the test compound or the test compound and either the non-adsorbed target protein or TLR9 protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of TLR9 binding or activity determined using standard techniques.

Other techniques for immobilizing either a TLR9 protein or a target molecule on matrices include using conjugation of biotin and streptavidin. Biotinylated TLR9 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemicals, Rockford, Ill.).

To conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with TLR9 protein or target molecules, but which do not interfere with binding of the TLR9 protein to its target molecule. Such antibodies can be derivatized to the wells of the plate, and unbound target or TLR9 protein trapped in the wells by antibody conjugation. Methods for detecting such complexes, in addition to those described above for the GST-immobilized complexes, include immunodetection of complexes using antibodies reactive with the TLR9 protein or target molecule, as well as enzyme-linked assays that rely on detecting an enzymatic activity associated with the TLR9 protein or target molecule.

Alternatively, cell-free assays can be conducted in a liquid phase. In such an assay, the reaction products are separated from unreacted components, by any of a number of standard techniques, including but not limited to: differential centrifugation (for example, Rivas, 1993, Trends Biochem. Sci. 18:284-287); chromatography (gel filtration chromatography, ion-exchange chromatography); electrophoresis (e.g., Ausubel et al., eds., 1999, Current Protocols in Molecular Biology, J. Wiley: New York.); and immunoprecipitation (for example, Ausubel et al., eds., 1999, Current Protocols in Molecular Biology, J. Wiley, New York). Such resins and chromatographic techniques are known to one skilled in the art (e.g., Heegaard, 1998, J. Mol. Recognit. 11: 141-148; Hage, 1997, J. Chromatogr. B. Biomed. Sci. Appl. 699:499-525). Further, fluorescence energy transfer may also be conveniently utilized, as described herein, to detect binding without further purification of the complex from solution.

In one embodiment, the assay includes contacting the TLR9 protein or biologically active portion thereof with a known compound that binds a TLR9 to form an assay mixture, contacting the assay mixture with a test compound, and determining the ability of the test compound to interact with a TLR9 protein. Determining the ability of the test compound to interact with a TLR9 protein includes determining the ability of the test compound to preferentially bind to TLR9 or biologically active portion thereof, or to modulate the activity of a TLR9, as compared to the known compound.

To identify compounds that interfere with the interaction between a TLR9 or fragment thereof (e.g., a TLR9 polypeptide that binds to a TLR9 ligand such as a CpG-DNA) and binding partner (e.g., a CpG-DNA), a reaction mixture containing the TLR9 or TLR9 fragment and the binding partner is prepared, and cultured under conditions and for a time sufficient, to allow the two products to form a complex. To test for a compound that interferes with binding between the TLR9 and the binding partner, the reaction mixture is provided in the presence and absence of the test compound. The test compound can be initially included in the reaction mixture, or can be added at a time subsequent to the addition of the TLR9 and its binding partner. Reference reaction mixtures are generally incubated without the test compound or with a compound that is known to be inactive (a control compound such as GpC-DNA). The formation of any complexes between the TLR9 and the binding partner are then detected. The formation of a complex in the reference reaction, but not in the reaction mixture containing the test compound, indicates that the compound interferes with the interaction of the TLR9 or TLR9 polypeptide and the binding partner. Additionally, complex formation within reaction mixtures containing the test compound and normal TLR9 or TLR9 fragment (that is, a sequence corresponding to a portion of a wild-type TLR9 protein) can also be compared to complex formation within reaction mixtures containing the test compound and a mutant TLR9 or polypeptide from a mutant TLR9. This comparison can be important in those cases in which it is desirable to identify compounds that disrupt interactions of mutant, but not normal TLR9 polypeptides.

These assays can be conducted in a heterogeneous or homogeneous format. Heterogeneous assays involve anchoring either the TLR9 polypeptide (e.g., full-length TLR9 or a fragment thereof) or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the TLR9 polypeptide and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the TLR9 (or fragment thereof) or the binding partner is anchored onto a solid surface (e.g., a microtiter plate), while the non-anchored species is labeled, either directly or indirectly. The anchored species can be immobilized by non-covalent or covalent attachments. Alternatively, an immobilized antibody that specifically binds to the species to be anchored (in this case, specifically binds means that the antibody does not significantly bind to any other component in the assay) can be used to anchor the species to the solid surface.

To conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the methods, a homogeneous assay can be used. For example, a preformed complex of the TLR9 (or fragment thereof) and the TLR9 binding partner is prepared in that either the TLR9 or the binding partner is labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt TLR9-binding partner interaction can be identified.

In another aspect, the methods include a combination of two or more of the assays described herein. For example, a compound that modulates the binding of a TLR9 to a CpG-DNA can be identified using a cell-based or a cell-free assay, and the ability of the agent to modulate the activity of a TLR9 protein can be confirmed in vitro or in vivo, e.g., in an animal such as an animal model for infection.

Also included herein are novel agents identified by the above-described screening assays. Accordingly, it is within the scope of this invention to further use an agent identified as described herein (e.g., a TLR9 modulating agent, a TLR9-specific antibody, or a TLR9-binding partner) in an appropriate animal model to determine the efficacy, toxicity, side effects, or mechanism of action, of treatment with such an agent. Furthermore, novel agents identified by the screening assays described herein can be used for treating disorders associated with TLR9-mediated signaling (to enhance or decrease TLR9 signaling, depending on the effect of the compound), for enhancing other physiological effects (e.g., as a vaccine adjuvant), or as a commercial product useful to study TLR9-related activity. For example, a compound that increases TLR9 signaling (a TLR9 agonist) is useful as an immunostimulant for use with therapeutic vaccines (e.g., cancer vaccines), an immunostimulant for use with prophylactic vaccines (e.g., hepatitis B vaccine), treatment of viruses (e.g., herpes simplex virus), and generally any condition in which it is desirable to enhance a TH1 immune response.

Test Compounds

The test compounds to be used in the methods described herein can be obtained using any method known in the art. For example, compounds can be obtained using any of the numerous approaches in combinatorial library methods known in the art, including: biological libraries; peptoid libraries (libraries of molecules having the functionalities of peptides, but with a novel, non-peptide backbone that are resistant to enzymatic degradation, but that nevertheless remain bioactive (e.g., Zuckermann et al., 1994, J. Med. Chem., 37:2678-2685); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, 1997, Anticancer Drug Des. 12:145).

Examples of methods for the synthesis of molecular libraries can be found in the art, for example in: DeWitt et al., 1993, Proc. Natl. Acad. Sci. U.S.A., 90:6909; Erb et al., 1994, Proc. Natl. Acad. Sci. U.S.A., 91:11422; Zuckermann et al.,1994, J. Med. Chem., 37:2678; Cho et al., 1993, Science, 261:1303; Carrell et al., 1994, Angew. Chem. Int. Ed. Engl., 33:2059; Carell et al.,1994, Angew. Chem. Int. Ed. Engl., 33:2061; and in Gallop et al., 1994, J. Med. Chem., 37:1233.

Libraries of compounds may be presented in solution (e.g., Houghten, 1992, Biotechniques, 13:412-421), or on beads (Lam, 1991, Nature, 354:82-84), chips (Fodor, 1993, Nature, 364:555-556), bacteria (Ladner, U.S. Pat. No. 5,223,409), spores (Ladner, U.S. Pat. No. 5,223,409), plasmids (Cull et al., 1992, Proc. Natl. Acad. Sci. U.S.A., 89:1865-1869), or on phage (Scott and Smith, 1990, Science, 249:386-390; Devlin, 1990, Science, 249:404-406; Cwirla et al., 1990, Proc. Natl. Acad. Sci. U.S.A., 87:6378-6382; Felici, 1991, J. Mol. Biol., 222:301-310; Ladner supra.).

Antibodies can be used as molecules that modulate TLR9-mediated signaling. Antibodies useful for such activity can interfere with the binding between TLR9 and a TLR9 ligand (such as a CpG) or the antibody can disrupt localization or TLR9 or a TLR9 ligand. Such antibodies can also be screening for their ability to inhibit or increase TLR9-mediated signaling. In general such antibodies are monoclonal antibodies. Methods of making such antibodies are known in the art.

Test compounds for modulation of TLR9 localization include compounds that decrease the ability of a CpG-DNA to stimulate TLR9 signaling. Such compounds can be CpG-DNA that is modified at the 5' end, a CpG-DNA having an altered C or G; modification of the CG flanking region, altering secondary structure of the CpG (e.g., by using oligonucleotides), or substitution, e.g., of a C, with a synthetic nucleoside.

Assays for TLR9-Mediated Signaling

In some embodiments, compounds are assayed for their ability to modulate TLR9-mediated signaling. Such assays can detect signaling at any point in the TLR9-mediated signaling pathway. For example, intracytoplasmic signaling events that can be detected include activation of p38, extracellular signal-regulated kinase (ERK, also known as mitogen-activated protein kinases (MAPKs)), and c-jun N-terminal kinase (JNK) pathways; Ikappa B kinase phosphorylation and activation; degradation of Iκα or Iκβ; or intracellular concentration of reactive oxygen species. Specific transcription factors can also be monitored to indicate signaling in the TLR9 pathway. For example, activation and nuclear translocation of the transcription NF-κB can be monitored. Nuclear translocation of NF-κB can also be monitored in localization assays simultaneously or in corresponding samples when testing compounds for the ability to modulate translocation of TLR9. Compounds that modulate (e.g., decrease) localization of TLR9 to the TLC are also expected to modulate (e.g., decrease) translocation of NF-κB to the nucleus. In some embodiments, TLR9-mediated signaling can be monitored by assaying the level of gene expression (e.g., mRNA levels). Examples of mRNAs that are increased during TLR9-mediated signaling include interferon (IFN)-alpha, IFN-beta, myc, myc-binding novel hlh/12 protein (myn or max), early growth response protein-1 (egr-1), c-jun, bcl-2, bcl-xL, tumor necrosis factor (TNF)-alpha, interleukin (IL)-6, IL-10 and IL-12. Assays of these RNAs can be performed in any cell type that expresses the mRNA in response to activation of TLR9-mediated signaling. Compounds that modulate TLR9-mediated signaling may also modulate expression of such mRNAs during induction by a TLR9 agonist (e.g., a CpG-DNA). In some cases, for example, when assaying components of the TLR9 signaling pathway that are also components of other, non-TLR9 signaling pathways, it is desirable to monitor such signaling in cells that express non-TLR9 TLRs, such as TLR1, 2, 3, 4, 5, 6, 7, or 8.

Other appropriate cellular responses can also be monitored. For example, activation of TLR9 by CpG-containing oligonucleotides in B cells results in cell proliferation, antibody secretion, modulation of RNA and protein expression, and secretion of IL-6 and IL-10. Activation also leads to the induction of the Fc gamma receptor, MHC class II, CD80, and CD86 on the cell surface. BCR-induced apoptosis is blocked in certain cells, e.g., WEHI-231 B cell line and primary B cells. Compounds that modulate TLR9 localization or binding that are useful for modulating TLR9-mediated signaling modulate these responses.

Cellular activation can also be monitored by reporter assays, such as assays utilizing the luciferase gene that is under the control of, e.g., NfκB or interferon responsive elements. Luciferase enzyme activity can be monitored in cellular lysates with methods known to the art.

Methods for performing assays for all of the above responses to TLR9-mediated signaling are known in the art. The ability of a compound to modulate such assays is readily assessed by testing the response in the presence and absence of a compound. An increase in the response indicates that the compound increases TLR9-mediated signaling. Such compounds are useful, e.g., to enhance the response to a vaccine. A decrease in the response indicates that the compound decreases TLR9-mediated signaling. Such compounds are useful, e.g., for decreasing an undesirable inflammatory response caused by activation of the innate immune system.

Animal Models

Animal models can be used to test compounds that have been identified based on their ability to modulate TLR9 binding to a TLR9 agonist (such as a CpG-DNA) or compounds that modulate localization of TLR9, CpG-DNA, or MD88. Animal models are particularly useful for determining the ability of such compounds to act as modulators of an immune response, for example, as adjuvants or inhibitors of a response as an inherent property. Such compounds can also be tested for their ability to decrease an immune or an inflammatory response. Examples of useful animal models include models of anthrax, influenza, herpes simplex, lymphocytic choriomeningitis virus, and plague infection have been developed in mouse, sheep, pig, and primate models (e.g., Williamson et al., 2002, Vaccine, 26:20(23-24):2933-2941, Dong et al., 2003, J. Gen. Virol., 84(Pt 6):1623-1628; Gierynska et al., 2002, J. Virol., 76:6568-6576; Oxenius, 1999, J. Virol., 73:4120-4126).

The invention is further illustrated by the following examples. The examples are provided for illustrative purposes only. They are not to be construed as limiting the scope or content of the invention in any way.

EXAMPLES

Reagents

Fluorescent transferrin, fluorescent dextran, DQ™-ovalbumin, ER-Tracker™ Blue White DPX, Mitotracker® Red, polyclonal anti-GFP antibody, and ethidium monoazide were obtained from Molecular Probes (Eugene, Oreg.). Polyclonal anti-calnexin antibody was from Stressgen (Victoria, BC). FITC-conjugated anti-calnexin monoclonal antibody, clone37, FITC-conjugated anti-EEA1 monoclonal antibody, clone14, and anti-GFP monoclonal antibody clone JL-8 were obtained from BD-Biosciences Transduction (Franklin Lakes, N.J.). Anti-human TLR9 monoclonal antibody eB72-1665 was from eBiosciences (San Diego, Calif.). The bacterial YFP-expression vector and sulfo-NHS-biotin were from Clontech, BD-Biosciences.

Example 1

Fluorescent TLR DNA Fusion Constructs

Fluorescent TLR protein chimeras were engineered as follows.

$TLR2^{YFP}$, $TLR4^{YFP}$, $TLR9^{CFP}$, $TLR9^{YFP}$, $TLR9^{GFP}$, and $MyD88^{CFP}$ and $MyD88^{YFP}$ constructs were created as follows.

The cDNA for human TLR4 was provided in the vector pcDNA3 by Drs. C. Janeway and R. Medzhitov (Yale University, New Haven, Conn.). The expression plasmid pRK7-TLR2 was obtained from Dr. C. Kirschning (Technical University of Munich). The vector pcDNA3 (Invitrogen) was previously modified to include either CFP or YFP as C-terminal epitope tags in frame with a cloning site (see Chan et al., 2000, J. Immunol. 165, 618-622). The same investigators also provided epitope-tagged p60 TNFR (Chan et al., 2000, supra). The hMD-2 mammalian expression plasmid pEFBOS containing C-terminal FLAG and His epitopes was a gift of Dr. K. Miyake (University of Tokyo). The Golgi subcellular localization vector consisting of the targeting sequence of human β-galactosyltransferase fused to CFP was purchased from CLONTECH.

Polymerase chain reaction of TLR2 and TLR4 was performed on pRK7-TLR2 and on pcDNA3-TLR4 in order to construct chimeric fluorescent cDNAs. The upper and lower primers for TLR2 were 5'-GAAGCAGGATCCATGCCA-CATACTTTGT-3' (SEQ ID NO:4) and 5'-GGGCTCGAGG-GACTTTATCGCAGCTCTCAGA-3' (SEQ ID NO:5). The upper and lower primers for TLR4 were 5'-GATGATG- GATCCATGATGTCTGCCTCGC-3' (SEQ ID NO:6) and 5'-ATTTTTGGCTCGAGGATAGATGTTGCTTCC-3' (SEQ ID NO:7). The primers for TLR9 were: 5'-GAAGCCCT-GCCCGGATCCATGGGTTTCTGC-3' (SEQ ID NO:8) and 5'-TCCGGCTCACTCGAGTTCGGCCGTGGGTCCCTG-3' (SEQ ID NO:9).

The TRL2 and TRL4 PCR fragments were digested with BamHI and XhoI and cloned in frame into pcDNA3-CFP and pcDNA3-YFP.

TLR9 PCR fragments were cloned into the BamHI and XhoI sites of pcDNA3-CFP, pcDNA3-YFP, and pcDNA3-GFP.

The fluorescent MyD88 constructs were made by PCR of MyD88 in pRK7 (provided by Dr. H. Wesche, Tularik, Inc., San Francisco, Calif.) using the following upper and lower primers for MyD88: 5'-CCACGGGGATCCATGGCTG-CAGGAGGTC-3' (SEQ ID NO:10) and 5'-GMAACAG-GTCGACGGGCAGGGACAAGGC-3' (SEQ ID NO:11). The PCR fragments were trimmed with BamHI and SalI and cloned in frame into pcDNA3-CFP or pcDNA3-YFP, respectively.

Retroviral constructs containing TLR9$^{YFP}$ and MyD88$^{CFP}$ were constructed similarly; PCR products were cloned into the plasmid Peak12mmpSfi-kilA (Randow et al., 2001, Nat. Cell Biol., 3:891-896).

Example 2

TLR9-Fluorescent Protein Chimeras are Functional Signaling Molecules

To use TLR fluorescent protein chimeras in screening assays and other protocols designed to examine TLR function and localization, it is necessary that the chimeras be able to act as functional TLRs. Accordingly, the engineered fluorescent TLR protein chimeras were tested for their ability to function in TLR signaling in cellular activation assays.

Cellular Activation Assays—Dual Luciferase Reporter Assays for NF-κB Activation

Cellular activation was assessed by NF-κB-luciferase reporter assay. Briefly, HEK293 cells that stably express TLR4$^{YFP}$, TLR2$^{YFP}$, TNFR$^{YFP}$, or empty vector (pcDNA) were seeded into 96-well tissue culture plates at a density of $2\times10^4$ cells/well. The following day, cells were transiently transfected with luciferase reporter genes using Genejuice (Novagen) per the manufacturer's recommendations. In order to assess NF-κB activation, an NF-κB-luciferase reporter gene consisting of an artificial promoter composed of a multimer of five NF-κB sites driving the firefly luciferase gene, was co-transfected with a constitutively active Renilla-luciferase reporter gene (Promega, Madison, Wis.).

The following day, the cells were stimulated as indicated. When necessary, HEK-TLR4$^{YFP}$ cells were either co-transfected with MD-2, stimulated in the presence of soluble MD-2 in conditioned medium, or retrovirally transduced with the cDNA for MD-2 (Visintin et al., 2001, Proc. Natl. Acad. Sci. U.S.A., 98:12156-12161). All three of these methodologies for expressing MD-2 comparably enhance TLR4-mediated responses to LPS. After 4-6 hours of stimulation, the cells were lysed in passive lysis buffer (Promega), and reporter gene activity was measured using a plate reader luminometer (Victor$^2$™; PerkinElmer Life Sciences) using the Dual-Luciferase Assay Reporter System (Promega) and normalized for transfection efficiency. In all cases, the data shown represent one of three separate experiments and are presented as the mean values±S.D. of triplicate samples.

It was found that all versions of fluorescently tagged TLR9, TLR fluorescent protein chimeras from full-length TLR cDNAs with the fluorescent proteins (CFP, GFP or YFP) fused to the C-terminus were fully functional signaling molecules that specifically recognized CpG-DNA when heterologously expressed in HEK cells.

These data demonstrate the utility of labeled TLRs, because immunological and direct fluorescent techniques can be used to track the TLR as it functions in a cell or associates with molecules in a cell or cell extract.

Example 3

TLR9-Fluorescent Protein Chimeras are Expressed in the ER

To determine the subcellular localization of TLR9, HEK cells expressing TLR9$^{GFP}$ were stained on the cell surface with a fluorescent membrane marker (cholera toxin subunit B, which binds to GM1 gangliosides present in lipid rafts; rhodamine-labeled choleratoxin subunit B was obtained from List Biological Laboratories (Campbell, Calif.)) and living cells were immediately examined using confocal microscopy.

An inverted Axiovert™ 100-M microscope equipped with a Zeiss LSM™ 510 META™ scanning unit using a 1.4 NA 63×plan apochromat objective (Zeiss, Jena, Germany) and an inverted Leica LSM™ TSC SP2™ Acousto-Optical Beam Splitter (AOBS™) were used for confocal observations. Cells were cultured on glass-bottom 35 mm tissue-culture dishes (Mattek, Ashland, Mass.). Dual or triple color images were acquired by consecutive scanning with only one laser line active per scan to avoid cross-excitation.

Figure 1A:
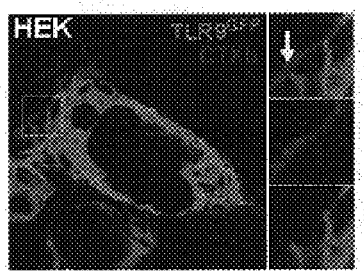
FIG. 1A is a set of confocal images of HEK-TLR9$^{GFP}$ cells (green) stained with choleratoxin subunit B (CTXB, red). The arrow shows contact of internal membranes (TLR9) with the plasma membrane.

TLR9 was expressed on a large pool of interconnected intracellular membranes. These intracellular membranes appeared to contact the plasma membrane in some areas (white arrow, FIG. 1A), but were not observed extending into the plasma membrane. The pattern of TLR9-fluorescent protein expression was similar in several different clones and different cell lines, indicating that the protein expression pattern is not specific for HEK cells. The expression pattern was consistent with the membranes that were highlighted by TLR9 representing the endoplasmic reticulum (ER).

Figure 1B:
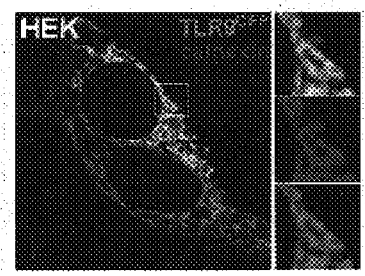
FIG. 1B is a set of confocal images of HEK-TLR9$^{CFP}$ cells (green) stained intracellularly for the ER protein calnexin (red).

To further investigate the localization of TLR9, HEK-TLR9$^{GFP}$ cells were permeabilized, fixed, and counterstained with a monoclonal antibody to calnexin, a resident protein of the ER. TLR9 and calnexin were observed to be expressed in the same intracellular pool of ER membranes (FIG. 1B). In addition, a cDNA construct containing the calreticulin ER-targeting sequence fused to YFP with TLR9$^{CFP}$ was co-transfected with the TLR9$^{CFP}$ construct. These cells were subjected to vital confocal microscopy, and complete colocalization was observed.

Figure 1C:
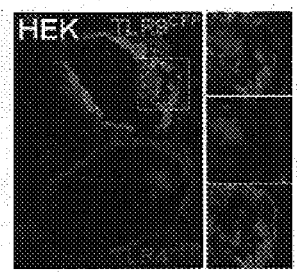
FIG. 1C is a set of confocal images of HEK-TLR4$^{YFP}$ cells (red) transiently transfected with TLR9$^{CFP}$ (green).

TLR4 is expressed on the plasma membrane and in the Golgi apparatus of transfected HEK cells and native human monocytes (Latz et al., 2002, supra). TLR9$^{CFP}$ was co-expressed in a cell line that stably expresses TLR4$^{YFP}$. Overlaid confocal microscopic images of the TLR9$^{CFP}$ and the TLR4$^{YFP}$ chimeric proteins failed to define any common area of expression (upper cell, FIG. 1C). Thus, using colocalization of TLR4 as a criterion of subcellular localization, TLR9 does not appear to be expressed in either the plasma membrane or the Golgi apparatus. Taken together, these data demonstrate that TLR9-fluorescent protein chimeras are expressed in the ER of quiescent HEK cells.

These data also demonstrate that localization of TLR9 can be used to determine whether a TLR9 construct (e.g., a mutant TLR9) is correctly localized. Similarly, localization of TLR9 or a TLR9 fusion protein can be used as an assay to determine whether a test compound affects localization of TLR9, as described herein. Compounds that affect TLR9 localization are expected to affect TLR9 signaling.

Example 4

Endogenous TLR9 is Expressed in the ER of Human Plasmacytoid Dendritic Cells (pDCs)

The possibility existed that the subcellular localization of fluorescently tagged TLR9 was due to the overexpression or misfolding of the genetically modified protein, despite the normal function of TLR9$^{YFP}$ as a CpG-DNA receptor. To investigate this possibility, the expression pattern of TLR9 in native cells by immunofluorescence studies of the endogenous protein was examined. The subcellular localization of TLR9 in human plasmacytoid dendritic cells (pDCs) was investigated because pDCs express high levels of messenger RNA for TLR9 and are activated by CpG-DNA (Hornung et al., 2002, J. Immunol., 168:4531-4537; Kadowaki et al., 2001, J. Exp. Med., 194:863-869). An anti-human TLR9 monoclonal antibody that specifically recognized heterologously expressed fluorescent TLR9 in HEK cells was used to stain endogenous TLR9 in pDCs.

In these experiments, pDCs were purified from blood mononuclear cells and matured in culture as described herein, and the cells were stained for endogenous TLR9.

Isolation and Culture of pDCs and DCs pDCs were purified from human PBMCs with anti-BDCA-4 coated microbeads (Miltenyi Biotech, Auburn, Calif.). Cells were consistently 95-98% pure as assessed by FACS. The pDCs were cultured in RPMI1640 supplemented with 10% FBS, 2 mM L-glutamine, 110 µg/ml sodium pyruvate, 10 µg of ciprofloxacin/ml, and 10 ng of IL-3/ml at a cell density of 5×10$^5$ cells/ml at 37° C. in 5% $CO_2$ for seven days.

In experiments employing retrovirally expressed fusion proteins, mouse bone-marrow derived DCs were used. These cells were obtained by incubating bone marrow cells with GM-CSF. IL-3 and GM-CSF were from Peprotech (Rocky Hill, N.J.).

Viral Transduction of Mouse DCs

To produce recombinant viruses, 293 T Ebna cells were cotransfected by calcium phosphate transfection with the TLR9$^{YFP}$ or MyD88$^{CFP}$ peak12 mmp plasmid and plasmids encoding the retroviral gag-pol genes and the envelope protein VSV-G and cultured for 24 hours. Virus-containing supernatant was prepared by centrifuging the cells at 250×g for 10 minutes. The supernatant was diluted 1:2 in cell culture medium and polybrene was added to a final concentration of 8 µg/ml. Mouse dendritic cells were derived from bone-marrow (Hemmi et al., Nature, 408:740-745) of C57BL/6 mice or MyD88$^{-/-}$ mice from a line backcrossed for five generations, and transduced on day two of culture.

CpG-ODN Uptake Assays

Phosphorothioate CpG-DNA was obtained from MWG Biotech (High Point, N.C.). DNA was labeled at the 3-prime end with either fluorescent tags or biotin. The sequences of stimulatory CpG-DNA were as published in Bauer et al. (2001, Proc. Natl. Acad. Sci. USA 98: 9237-9242). At day seven after isolation, adherent pDCs were incubated with 3 mM fluorescent CpG-DNA in growth medium for various time periods. Washed cells were immediately imaged using confocal microscopy at 37° C. Fluorescent CpG-DNA (3 µM) was co-incubated with fluorescent transferrin or human albumin (10 µg/ml). The lysosomal compartment in dendritic cells was labeled by incubating cells with 250 µg/ml fluorescent dextran for 30 minutes as described in Chow et al. (2002, Nature, 418:988-994). Alternatively, cells were incubated with DQ-ovalbumin (5 µg/ml) for 30 minutes before imaging.

Immunofluorescence

Cells were either fixed by incubation in PBS containing 2% freshly prepared paraformaldehyde at room temperature for 20 minutes or by incubation in 100% methanol at −20° C. for 60-90 seconds. Cells were washed extensively and non-specific antibody binding sites were blocked with phosphate-buffered saline (PBS) containing 0.25% saponin, 1% bovine serum albumin (BSA), and 2.5% human serum for 15-30 minutes at 20° C. Staining was done by incubating the cells with the antibody in blocking buffer at 25° C. for 45 minutes followed by washes and incubation in labeled secondary antibody according to known procedures.

Figure 1D:
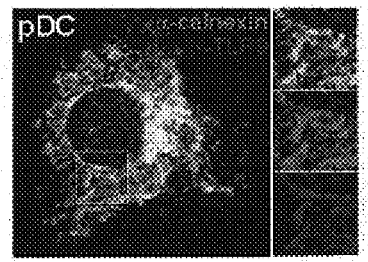
FIG. 1D is a set of confocal images of plasmacytoid dendritic cells (pDCs) that were co-stained intracellularly with anti-TLR9 monoclonal antibody (red, Alexa 647) and anti-calnexin monoclonal antibody (green, FITC).
Figure 1E:
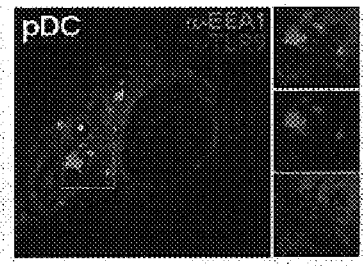
FIG. 1E is a set of confocal images of pDCs that were stained with anti-TLR9 monoclonal antibody (red, Alexa 647) and anti-EEA1 (early endosomal antigen 1) monoclonal antibody, an early endosome marker (green, FITC).
Figure 1F:
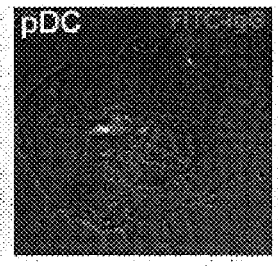
FIG. 1F is a confocal image of pDCs that were stained with directly conjugated reference Abs.

Confocal microscopic studies demonstrated intracellular staining of TLR9. The cells were counterstained for the ER resident protein calnexin. The observed colocalization of the fluorescent signal revealed that endogenous TLR9 is expressed in the ER of native pDCs (FIG. 1D). A marker protein for early endosomes (EEA1) did not colocalize with TLR9 in resting cells (FIG. 1E) and isotype-matched reference monoclonal antibodies did not significantly stain pDCs (FIG. 1F).

These data demonstrate that the localization of TLR9 is in the ER of both (1) a cell type in which a TLR9 construct is expressed and (2) a cell type that expresses endogenous TLR9, thus supporting the detection of localization of TLR9 or TLR9 fusion proteins for assays related to the localization of TLR9, e.g., assays for identifying compounds or TLR9 mutations that affect TLR9 localization and thereby are candidate compounds for modulating TLR9 function.

Example 5

CpG-DNA Enters Plasmacytoid Dendritic Cells (pDCs) via Early Endosomes and Traffics into a Tubular Lysosomal Compartment Since the effector for TLR9-mediated signaling is CpG-DNA, experiments were performed to investigate the uptake pathway and trafficking of CpG-DNA in cells, and to see if CpG-DNA moved to the same compartment in which TLR9 was expressed.

Adherent pDCs were incubated with fluorescent CpG-DNA for various time periods, and after washing, the cells were observed using confocal microscopy at 37° C.

When cells were incubated with labeled CpG-DNA for a short time period (FIGS. 2A-C, 5 minutes), small vesicular structures were observed in the cell periphery. These structures travelled toward the center of the cells. Colocalization studies of cells co-incubated with CpG-DNA and fluorescent transferrin revealed that these structures were early endosomes (FIGS. 3A-D). Similarly, these structures were labeled with the phosphatidyl-inositol-3-phosphate (PI3P) binding construct FYVE-GFP (Stenmark, 2002, FEBS Lett., 513:77-84), a marker for early endosomes (FIGS. 3E-H). CpG-DNA-positive vesicles did not contain caveolin-1, and failed to colocalize with human albumin, indicating a caveolin-independent uptake pathway (FIGS. 3I-L and 3M-P).

Figure 2A:
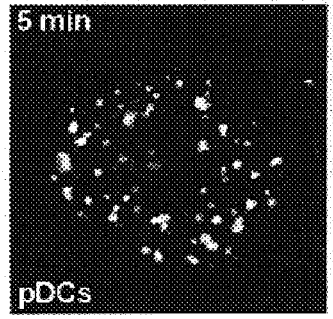
FIGS. 2A-C are confocal images of pDCs that were incubated with fluorescent CpG-DNA for the indicated time points and imaged by confocal microscopy.
Figure 2B:
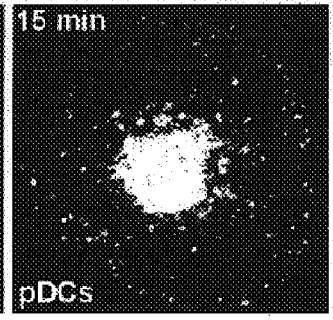
Figure 2C:
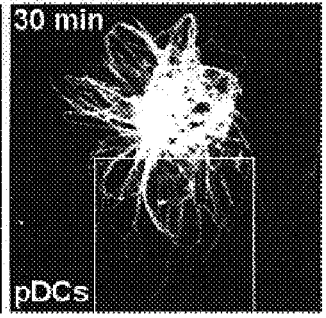
Figure 2D:
FIGS. 2D-H are individual frames obtained by time-lapse confocal microscopy of a cell incubated for 30 minutes with CpG-DNA (white box in FIG. 2C).
Figure 2E:
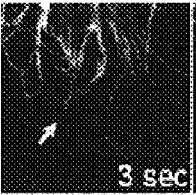
Figure 2F:
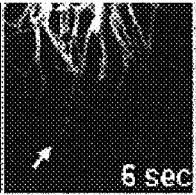
Figure 2G:
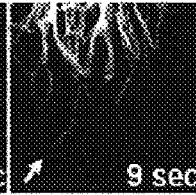
Figure 2H:
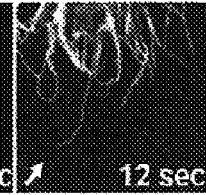
Figure 7A:
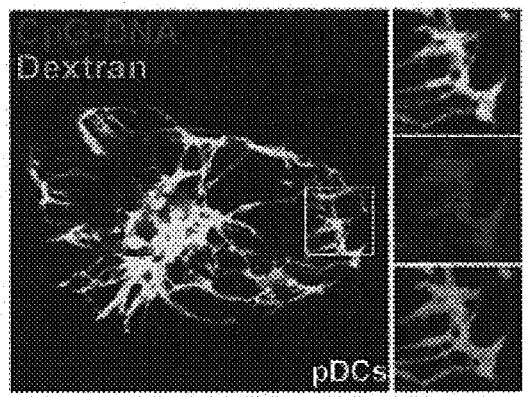
FIG. 7A is a set of confocal images of pDCs that were co-incubated with fluorescent CpG-DNA (red) and fluorescent dextran (green).
Figure 7B:
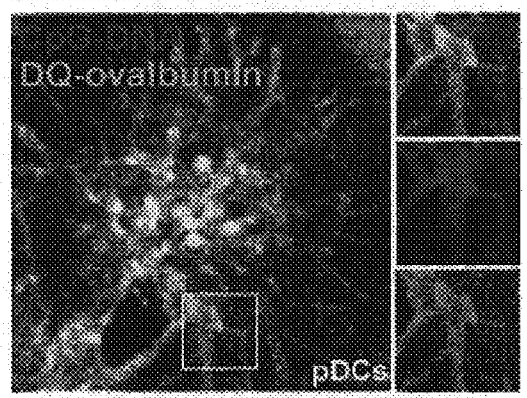
FIG. 7B is a set of confocal images of pDCs that were incubated with DQ-ovalbumin (green) for 30 minutes before imaging.
Figure 7C:
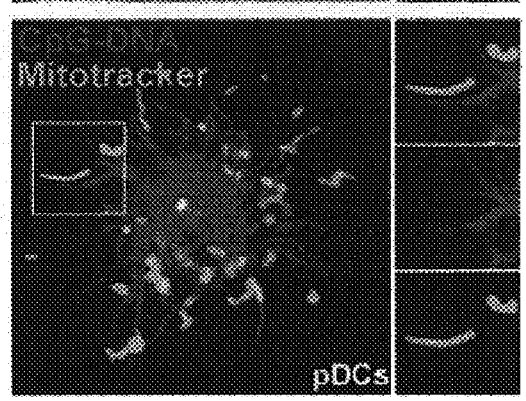
FIG. 7C is a set of confocal images of pDCs that were incubated with CpG-DNA (red) and counterstained with a mitochondrial marker (green).

After 10 to 15 minutes of incubation, many of the DNA-positive vesicles were concentrated in juxtanuclear areas (FIG. 2B, 15 minutes). Tubular structures filled with CpG-DNA began to appear as early as 15 minutes after exposure. By 30 minutes of incubation, almost all the CpG-DNA was localized in large tubular structures (FIG. 2C, 30 minutes). The tubules were highly motile and could be observed extending towards the cell periphery and plasma membrane and then retracting back again towards the cell center every 10-15 seconds. In FIGS. 2D-H, a short sequence extracted from a confocal time-lapse is shown from a cell that was exposed to labeled CpG-DNA for 30 minutes. This study highlights the motility of the observed tubular structures containing CpG-DNA (FIGS. 2D-H, white arrows). Colocalization studies of CpG-DNA and fluorescent dextran or DQ-ovalbumin identified these structures as the tubular lysosomal compartment (FIGS. 7A-7C). These results demonstrate that CpG-DNA and TLR9 colocalize to the TLC.

Example 6

CpG-DNA Binds to TLR9

To address the question whether the trafficking of CpG-DNA into cells was related to TLR9 signal transduction, confocal studies of HEK-TLR9$^{CFP}$ cells exposed to CpG-DNA was performed. It was found that TLR9 was actively recruited to CpG-DNA containing cellular structures from the ER (discussed in detail below for primary cells). These intense contact areas appear to be areas of ligand-receptor interaction. Thus, compounds that interfere with TLR9-ligand interactions are generally compounds that can enter the intracellular structures in which TLR9 interacts with its ligand. Such compounds can bind with TLR9 or the TLR9 ligand in a separate compartment from the final cellular compartment in which TLR9 and the ligand interact.

Ligand binding studies were performed on stably transfected HEK cell lines. Monolayers of HEK cells expressing chimeric TLR9$^{YFP}$ or TLR4$^{YFP}$ were incubated for 8 hours with 5 μM biotinylated CpG-DNA 2006, which is known to stimulate human TLR9, or the biotin-labeled non-stimulatory GpC-DNA oligonucleotide 2006GC, before lysis and were then microcentrifuged to remove nuclear debris. Cells were lysed in passive lysis buffer (Promega, Madison, Wis.). Alternatively, clarified cellular lysates were incubated with 5 μM biotinylated CpG-DNA. Streptavidin-coated beads (25 μl of a 50% suspension) were added to 500 μl of lysate and rotated for 1 hour at 4° C. In some cases, lysates were incubated with anti-GFP polyclonal antibody and 40 μl of packed protein A-Sepharose™ at 4° C. for 1 hour to assess the overall protein levels of chimeric TLRs. Pellets were washed four times in lysis buffer, resolved by SDS-PAGE, and transferred to nitrocellulose membranes (HyBond™ C, Amersham Biosciences). Membranes were blocked in 5% powdered milk and blotted with anti-GFP monoclonal antibody. Blots were then incubated with HRP-conjugated anti-mouse antibody and developed on Hyperfilm™ with the enhanced chemiluminescence horseradish peroxidase (HRP) substrate system (Amersham Biosciences).

Figure 4A:
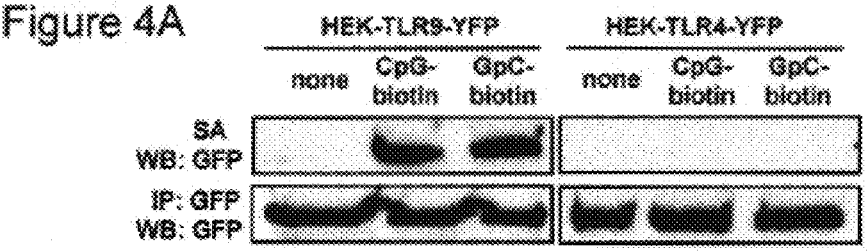
FIG. 4A is a reproduction of a Western blot depicting the results of an experiment in which HEK-TLR9$^{YFP}$ or HEK-TLR4$^{YFP}$ cells were incubated with biotin-CpG-DNA (2006, Adams et al., Nucleic Acids Res., 2000, 28(21):4244-53) or biotin-GpC-DNA (2006GC) for eight hours at 37° C. Biotin-DNA was then precipitated from lysates and associated proteins analyzed by Western (GFP) for TLRs. SA indicates streptavidin precipitation of the sample. WB indicates Western blot and the letters after WB indicate the detection method. GFP indicates that an anti-GFP antibody (that cross-reacts with YFP) was used for detection.

After eight hours, the cells were lysed and the biotinylated DNA was precipitated using streptavidin-coated beads. Western blotting demonstrated that both the stimulatory and non-stimulatory DNA bound and captured TLR9 (FIG. 4A, left panel). In contrast, neither CpG-DNA (2006) nor GpC-DNA (2006GC) bound and precipitated TLR4$^{YFP}$ (FIG. 4A, right panel). These data demonstrate an example of a compound (2006GC) that can bind to TLR9 and does not stimulate TLR9-mediated signaling. This demonstrates an assay that can be used to identify other compounds that can bind to TLR9.

Figure 4B:
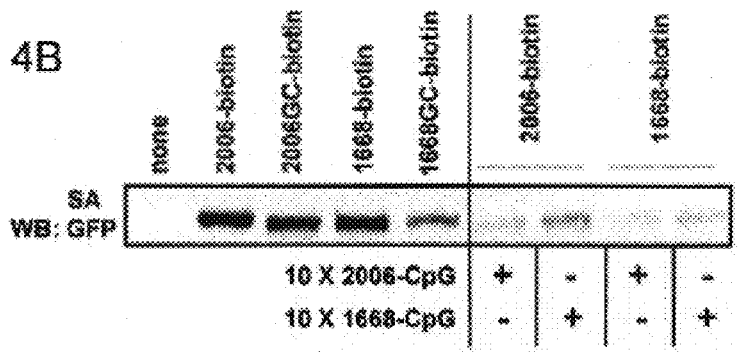
FIG. 4B is a reproduction of a Western blot depicting the results of an experiment in which HEK-TLR9$^{YFP}$ lysates were incubated with different biotinylated CpG-oligonucleotides: sequence 2006 is stimulatory for hTLR9 (2006GC) and 1668 optimally stimulates mTLR9 (1668GC, Whitmore et al., Cancer Immunol. Immunother., 2001, 50(10):503-14). After one hour, biotinylated CpG-DNA was precipitated with streptavidin (SA) and proteins were analyzed by Western blot (WB) using anti-GPP antibody (GFP). A ten-fold excess of non-labeled CpG-DNA was added to identically treated samples (right panel).

To eliminate the role of DNA uptake from the binding assay, cellular lysates of TLR9$^{YFP}$ and TLR4$^{YFP}$ expressing HEK cells were prepared and both stimulatory CPG- and non-stimulatory GPC-DNA were added at 4° C. Consistent with the previous results, streptavidin precipitation and Western blotting revealed that both types of oligonucleotides bound to TLR9, but not to TLR4. Similarly, TLR9 binding of labeled oligonucleotides that were optimized for mouse TLR9 and their counterpart non-stimulatory GpC-DNA sequences (1668, 1668GC) was tested. All versions of the biotinylated CpG- or GpC-DNA bound and precipitated human TLR9 (FIG. 4B). Thus, CpG-DNA directly binds to TLR9 in a CG-sequence independent manner. When the cellular lysates of TLR9$^{YFP}$ expressing cells were simultaneously incubated with biotinylated CpG-DNA and a ten-fold excess of unlabeled oligonucleotides, competitive inhibition was observed (FIG. 4B), indicating that the observed binding was saturable.

Figure 4C:
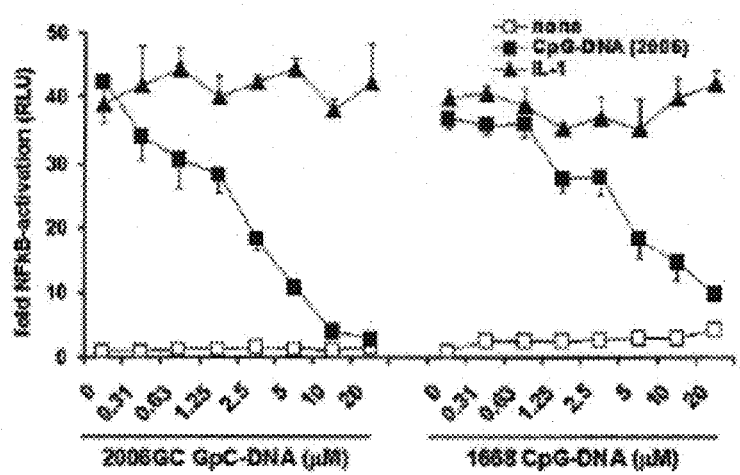
FIG. 4C is a pair of graphs depicting the results of experiments in which HEK-TLR9 cells were treated with 1 μM CpG-DNA or IL-1 (100 ng/ml) in presence of increasing doses of non-stimulatory GpC-DNA (2006GC) or mTLR9-optimized CpG-DNA (1668GC). Cellular activation was assessed by luciferase measurements and plotted as relative luciferase units (RLU).

To determine whether the observed binding of TLR9 to various oligonucleotides predicted the ability of each construct to induce inflammatory responses, oligonucleotides were tested in cell stimulation assays. In these experiments, TLR9-expressing HEK cells were incubated with CpG-DNA alone or together with increasing concentrations of non-stimulatory GpC-DNA (2006GC) or the mouse optimized CpG-DNA (1668), and NF-κB activation was assessed. Both, GpC-DNA 2006GC (FIG. 4C, left panel) and CpG-DNA 1668 (FIG. 4C, right panel) potently inhibited TLR9-mediated signaling. Neither oligonucleotide inhibited IL-1 signaling. These data illustrate another aspect of the methods described herein; they can be used to identify compounds with the ability to modulate TLR9-mediated signaling. The use of a type of reference (e.g., a control such as TLR4 and monitoring IL-1) is also demonstrated.

Example 7

TLR9 and MyD88 are Recruited to the Same Compartment as CpG-DNA

Figure 5A:
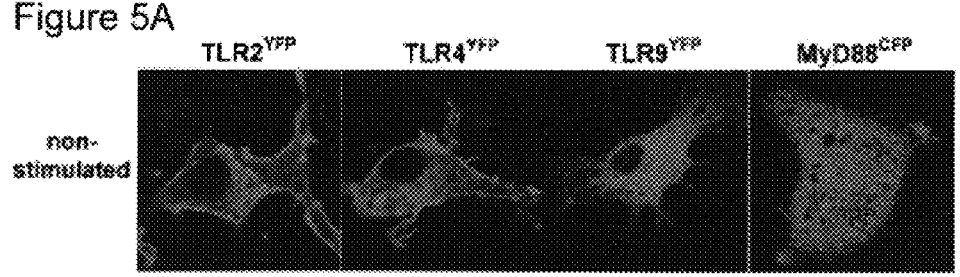
FIG. 5A is a set of confocal images of mouse bone-marrow derived DCs expressing TLR2$^{YFP}$, TLR4$^{YFP}$, TLR9$^{YFP}$, or MyD88$^{CFP}$ that were left untreated (none) for the indicated times.
Figure 8A:
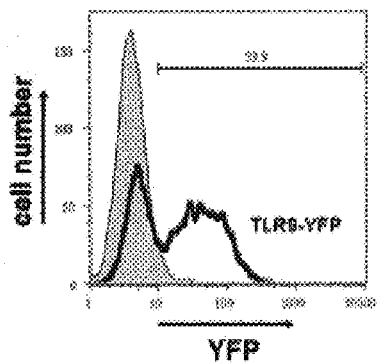
FIG. 8A is a graph depicting the results of flow cytometry in which mouse DCs were transduced with retroviral TLR9$^{YFP}$ and analysed by flow cytometry.
Figure 8B:
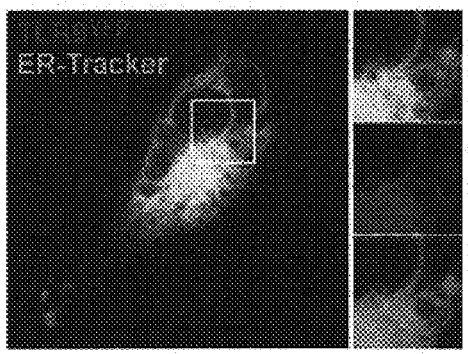
FIG. 8B is a set of confocal images of mouse DCs that expressed TLR9$^{YFP}$ and were incubated with a marker for endoplasmic reticulum (ER Tracker).
Figure 8C:
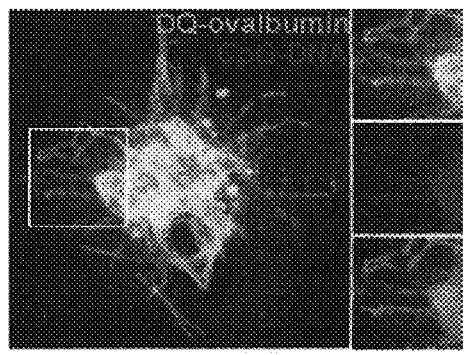
FIG. 8C is a set of confocal images of mouse DCs that were co-incubated with fluorescent CpG-DNA and DQ-ovalbumin for 30 minutes before collecting the images.
Figure 8D:
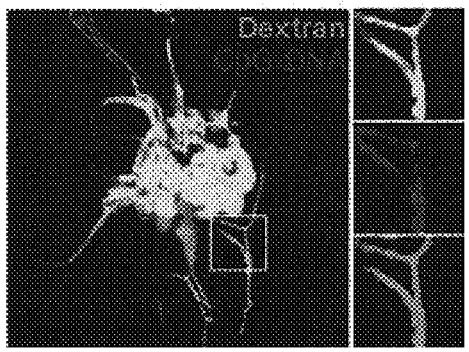
FIG. 8D is a set of confocal images of mouse DCs that were co-incubated with fluorescent dextran for 30 minutes before collecting the images.

To investigate the spatial behavior of TLR9 and the adapter protein MyD88 upon treatment with CpG-DNA, mouse bone marrow-derived dendritic cells (DCs) and macrophages were transduced with a retroviruses carrying a gene that can express a fluorescent TLR9 (FIGS. 5A-C and FIG. 8A). In resting native immune cells, TLR9$^{YFP}$ was expressed in the ER (FIG. 5A and FIG. 8B), similar to human HEK-TLR9$^{FP}$ cells and human pDCs. In contrast, YFP-tagged TLR2 and TLR4 were both expressed on the surface of mouse DCs (FIG. 5A). A fluorescent hybrid protein, MyD88$^{CFP}$, was ubiquitously expressed in the cytoplasm of resting cells (FIG. 5A). Note that TLR2 and TLR4 both recycle from the cell surface to the Golgi apparatus in resting cells, accounting for the intracytoplasmic accumulations of fluorescence that are visible upon close inspection.

Figure 5B:
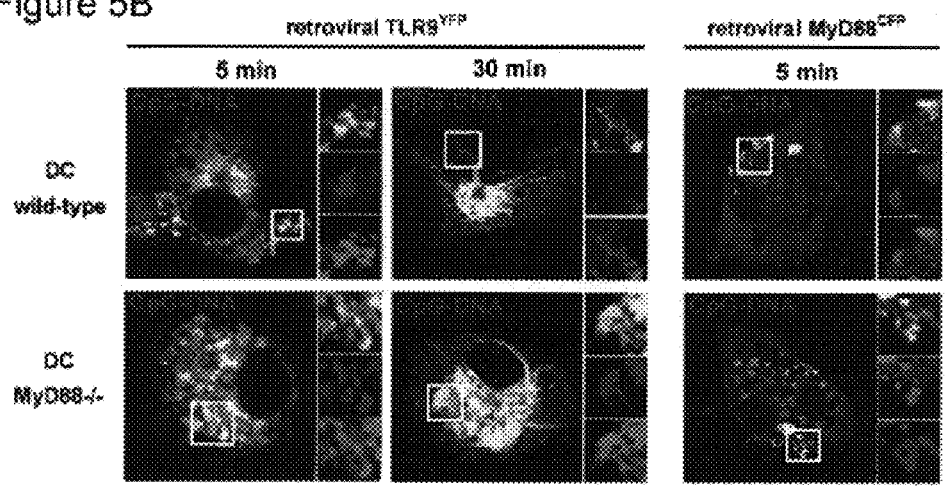
FIG. 5B is a set of confocal images of mouse DCs expressing TLR9$^{YFP}$ or MyD88$^{CFP}$ that were incubated with fluorescent CpG-DNA for the indicated times. DCs isolated from wild-type (upper panel) or MyD88$^{-/-}$ mice (lower panel) were transduced with retroviruses containing TLR9$^{YFP}$ or MyD88$^{CFP}$. Cells were incubated with fluorescent CpG-DNA for the indicated time periods and living cells were analyzed by confocal microscopy.

When TLR9 YFP-expressing mouse DCs were incubated with fluorescent CpG-DNA, the trafficking behavior of CpG-DNA was observed to be identical to that observed in human pDCs (FIGS. 5B upper panel, 8C and 8D). In addition, a rapid reorganization of TLR9$^{YFP}$ towards the cell entry sites of CpG-DNA was observed. Extensive colocalization of TLR9$^{YFP}$ with CpG-DNA was observed in these areas as early as five minutes after the addition of CpG-DNA (FIG. 5B upper panel). Furthermore, MyD88 was also recruited to the entry site of CpG-DNA in a similarly rapid time frame (FIG. 5B upper panel). After longer incubations, CpG-DNA moved into tubular lysosomal structures that also contained TLR9$^{YFP}$.

Figure 5C:
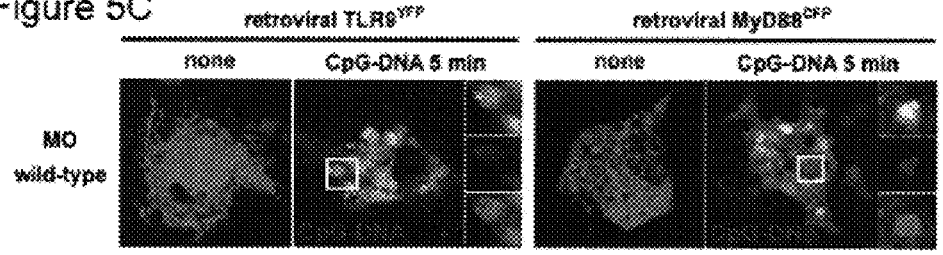
FIG. 5C is a set of confocal images of mouse macrophages expressing TLR9$^{YFP}$ or MyD88$^{CFP}$ that were incubated with CpG-DNA for five minutes or left untreated (none).

The observed movement of TLR9 and MyD88 to CpG-DNA-containing structures was retained in DCs derived from MyD88-null mice (FIG. 5B, lower panels). Similar redistributions of TLR9$^{YFP}$ and MyD88$^{CFP}$ were observed in mouse macrophages (FIG. 5c). These results suggested that TLR9 is localized in the ER in resting cells and is rapidly recruited to the sites of CpG-DNA accumulation in a MyD88-independent manner.

To investigate whether endogenous TLR9 redistributed in a similar pattern as heterologously expressed fluorescent TLR9, human pDCs were incubated with fluorescent CpG-DNA and TLR9 was visualized by direct immunofluorescence. TLR9 was recruited—as was its fluorescent counterpart—to CpG-DNA as early as five minutes after incubation, and followed CpG to intracellular compartments. In contrast, when pDCs were incubated with fluorescent transferrin, which also resulted in the formation of early endosomes, no colocalization of TLR9 with transferrin was observed (FIG. 6A). When resting pDCs were co-stained for TLR9 and an early endosome marker protein (EEA1), TLR9 was excluded from the early endosome compartment. However, as early as five minutes after CpG-DNA stimulation, a significant portion of TLR9 was detected in a EEA1-positive compartment (FIG. 6B). These observations indicate the specificity of this translocation event.

Next, the mechanism by which TLR9 reaches the endosomal compartment from the ER after stimulation was investigated. One possibility was that TLR9 could be released from the ER to reach the endosomal pathway via passage through the Golgi apparatus. Proteins that are targeted to the plasma membrane are normally released from the ER and traffic through the Golgi apparatus in a pathway termed the secretory pathway. To test whether TLR9 enters the secretory pathway the two glycosidases: endoglycosidase H (Endo H) and peptide:N-glycosidase F (PNGase F), were used. PNGase F cleaves all ER- and Golgi-derived carbohydrate modifications, while Endo H loses its ability to cleave carbohydrate species once they have been modified by Golgi-localized enzymes (Helenius and Aebi, 2001, Science, 291: 2364-2369). Endoglycosidase H and peptide:N-glycosidase F were purchased from New England Biolabs (Beverly, Mass.).

Resting or CpG-stimulated cells grown on tissue culture dishes were cooled on ice, washed three times with ice-cold Hank's Balanced Saline Solution (HBSS), and incubated with 1 mg Sulfo-NHS-Biotin per ml HBSS for 30 minutes on ice. After two washes with ice-cold HBSS, free reactive biotin was quenched by incubation with ice-cold 1M Tris HCL (pH 8.0) for five minutes. Subsequently, the cells were lysed in lysis buffer and fluorescently tagged TLR4$^{YFP}$ and TLR9$^{YFP}$ were immunoprecipitated using anti-GFP. Biotin immunoreactivity was assessed by Western blot and detection using an anti-biotin HRP conjugated antibody. The membranes were stripped and reprobed with anti-GFP antibody to assess the total expression of the TLRs.

The glycosylation state of TLRs was assessed by incubating immunoprecipitated and denatured TLR9 or TLR4 (via anti-GFP antibody) with endoglycosidase H or peptide:N-glycosidase F for 1 hour at 37° C. The proteins were separated by SDS-gel electrophoresis and electrophoretic mobility was assessed by Western Blotting and detection of GFP.

Subsequently, the molecular weights of the treated proteins were investigated by SDS-PAGE followed by Western blotting. PNGase F treatment resulted in the complete cleavage of the carbohydrate modifications of both TLR4$^{YFP}$ and TLR9$^{YFP}$ (FIG. 6C, "F"). In contrast, only a fraction of the TLR4$^{YFP}$ molecules were cleaved by Endo H treatment, indicating that TLR4$^{YFP}$ enters the secretory pathway. Conversely, all of the carbohydrate modifications of TLR9 were cleaved by Endo H (FIG. 6C, "H"). Thus, TLR9 does not enter the secretory pathway. The lack of TLR9 expression in the Golgi, observed by confocal microscopy, (FIG. 1C) correlates with the complete Endo H sensitivity of TLR9. TLR9 was observed to move out of the ER in CpG-DNA stimulated cells. However, TLR9 never acquired Endo H resistance in stimulated cells, providing evidence against a role of the secretory pathway for TLR9 redistribution to CpG-DNA containing compartments. Thus, when selecting compounds to test for their ability to modulate TLR9 activity or localization, compounds that affect the secretory pathway are not desirable test or candidate compounds.

Figure 6D:
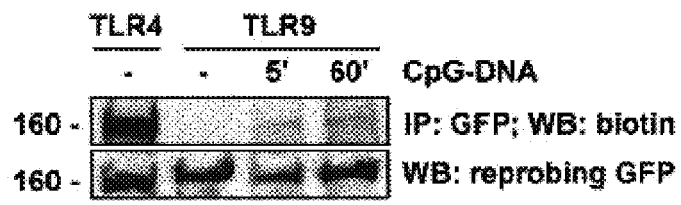
FIG. 6D is a reproduction of a Western blot from an experiment in which HEK-TLR4$^{YFP}$ or HEK-TLR9$^{YFP}$ cells were left untreated (−) or stimulated with CpG-DNA (2006, 1 μM) for the indicated time periods. Cooled cells were surface biotinylated and total TLRs were immunoprecipitated using an anti-GFP antibody and subjected to SDS-gel electrophoresis. Membranes were probed for biotin (top panel) and reprobed for TLRs (using anti-GFP antibody).

An alternative explanation for the observation that TLR9 translocates to CpG-DNA-containing compartments is that the ER could fuse with the plasma membrane and contribute its membranes to the developing endosomes. During these fusion events ER proteins may leak onto the plasma membrane in small quantities, as has been observed for the ER-resident protein calnexin. To test this possibility, HEK-TLR9$^{YFP}$ cells that were either left untreated or were stimulated with CpG-DNA were surface biotinylated using known methods. After CpG-stimulation, a small portion of the total TLR9 (FIG. 6D) expressed in these cells became surface accessible, as evidenced by the acquisition of biotin.

These results indicate that the methods described herein can be used to identify compounds that affect localization of TLR9 to a specific compartment.

Example 8

Study of TLR9 Receptor Homo-Multimerization Caused by CpG-DNA

To further evaluate the effects of CpG-DNA treatment, aggregation of TLR9 was evaluated using Fluorescence Resonance Energy Transfer (FRET). A mixture of stably transfected HEK-TLR9-CFP (FIGS. 9A-B, green), HEK-TLR9-YFP (9A-B, red) and HEK-TLR9-CFP/TLR9-YFP (9A-B, yellow) cells was grown on glass-bottom tissue culture dishes and either left untreated (FIGS. 9A and 9C) or stimulated with CpG-DNA (2006 sequence; FIGS. 9B and 9D). The areas of highest intensity (red, FIGS. 9C-D) represent FRET that has been induced by endosomal CpG-DNA. After addition of CpG-DNA, TLR9 translocates from the endoplasmic reticulum to an endosomal compartment (FIGS. 9A-B), and aggregation of TLR9, resulting in the formation of TLR9 multimeric complexes that result in increased FRET (FIGS. 9C-D). FIG. 9 illustrates that the addition of CpG-DNA also leads to TLR9 aggregation within the endosomal compartment. FRET was analyzed by using the sensitized emission formula: FRET=B−b×A−(c−a×b)×C, where A=donor emission (by excitation of the donor), B=FRET emission (by excitation of the donor) and C=acceptor emission (by excitation of the acceptor), a, b, and c are correction factors to account for crossexcitation and spectral bleedthrough. Single positive TLR9 cells served as internal negative references for FRET.

These results indicate that the methods described herein can be used to identify compounds that affect aggregation of TLR9, e.g., aggregation within the endosomal compartment.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of identifying a compound that modulates Toll-Like Receptor 9 (TLR9) signaling, the method comprising:
   (a) providing a living cell that expresses a fluorescently-tagged TLR9 polypeptide;
   (b) contacting the cell with a test compound, thereby providing a test sample;
   (c) incubating the test sample under conditions and for a period of time, which conditions and period of time are sufficient for TLR9 polypeptide localization, translocation, and/or aggregation to occur in a reference sample that lacks the test compound; and
   (d) detecting in said living cell one or more TLR9 polypeptide characteristics selected from the group consisting of: rate of TLR9 polypeptide localization, rate of TLR9 polypeptide translocation, and combinations thereof,
   wherein a difference in the one or more TLR9 polypeptide characteristic characteristics in the test sample compared to the one or more TLR9 characteristic characteristics in the reference sample indicates that the test compound is a compound that modulates TLR9 signaling.

2. The method of claim 1, wherein the test sample and reference sample further comprise a TLR9 ligand.

3. The method of claim 2, wherein the TLR9 ligand is a CpG-DNA.

4. The method of claim 1, wherein the TLR9 polypeptide is a fusion protein.

5. The method of claim 1, wherein the TLR9 polypeptide is a fusion protein comprising a Yellow Fluorescent Protein (YFP), a Cyan Fluorescent Protein (CFP), Green Fluorescent Protein (GFP), Red Fluorescent Protein (RFP), or a fluorescent variant thereof.

6. The method of claim 1, wherein said difference in one or more TLR9 polypeptide characteristics is a difference in the rate of TLR9 polypeptide localization.

7. The method of claim 1, said difference in the one or more TLR9 polypeptide characteristics is a difference in the rate of TLR9 polypeptide translocation.

8. The method of claim 1, wherein following step (c), the cell is fractionated and fractions are tested for the presence of TLR9 polypeptide.

9. The method of claim 1, wherein the TLR9 polypeptide comprises a full-length TLR9 protein.

10. The method of claim 1, wherein the TLR9 polypeptide comprises a fragment of TLR9 comprising one or more regions selected from the group consisting of: LRR region 1, LRR region 2; transmembrane domain; Toll/IL-1 Resistance (TIR) domain; a ligand binding domain; and a localization signal domain.

11. The method of claim 10, wherein the ligand binding domain comprises one or more CXXC motifs.

12. The method of claim 11, wherein the CXXC motif is CRRC (amino acids 255-258 of SEQ ID NO:1) or CMEC (amino acids 265-268 of SEQ ID NO:1).

13. The method of claim 1, wherein the test compound is a modified CpG-DNA.

* * * * *

UNITED STATES PATENT AND TRADEMARK OFFICE
CERTIFICATE OF CORRECTION

| | |
|---|---|
| PATENT NO. | : 7,723,054 B2 |
| APPLICATION NO. | : 11/341319 |
| DATED | : May 25, 2010 |
| INVENTOR(S) | : Eicke Latz et al. |

It is certified that error appears in the above-identified patent and that said Letters Patent is hereby corrected as shown below:

Column 51, line 19 should read:

"characteristics in the test sample" and delete "characteristic"

Column 51, line 20 should read:

"to the one or more TLR9 characteristics" and delete "characteristic"

Signed and Sealed this

Fourteenth Day of September, 2010

David J. Kappos
*Director of the United States Patent and Trademark Office*